United States Patent
Lee et al.

(10) Patent No.: US 11,779,582 B2
(45) Date of Patent: Oct. 10, 2023

(54) COMPOSITION FOR PREVENTING OR TREATING METASTATIC OVARIAN CANCER, ENDOMETRIAL CANCER OR BREAST CANCER

(71) Applicant: LEMONEX INC., Seoul (KR)

(72) Inventors: Jae Ho Lee, Gyeonggi-do (KR); Cheolhee Won, Seoul (KR)

(73) Assignee: LEMONEX INC., Seoul (KR)

( * ) Notice: Subject to any disclaimer, the term of this patent is extended or adjusted under 35 U.S.C. 154(b) by 24 days.

(21) Appl. No.: 16/476,220

(22) PCT Filed: Jan. 8, 2018

(86) PCT No.: PCT/KR2018/000379
§ 371 (c)(1),
(2) Date: Jul. 5, 2019

(87) PCT Pub. No.: WO2018/128510
PCT Pub. Date: Jul. 12, 2018

(65) Prior Publication Data
US 2021/0137922 A1    May 13, 2021

(30) Foreign Application Priority Data

Jan. 6, 2017 (KR) .................. 10-2017-0002180
Jan. 8, 2018 (KR) .................. 10-2018-0002491

(51) Int. Cl.
*A61K 31/506* (2006.01)
*A23L 33/10* (2016.01)
(Continued)

(52) U.S. Cl.
CPC ............ *A61K 31/506* (2013.01); *A23L 33/10* (2016.08); *A61K 31/165* (2013.01);
(Continued)

(58) Field of Classification Search
CPC .. A61K 31/506; A61K 31/475; A61K 31/165; A61K 31/337; A61K 31/343;
(Continued)

(56) References Cited

U.S. PATENT DOCUMENTS

| 2010/0160348 A1* | 6/2010 | Matei ............... G01N 33/57449 514/260.1 |
| 2011/0177062 A1* | 7/2011 | Floch .................. C07K 16/303 424/133.1 |

(Continued)

FOREIGN PATENT DOCUMENTS

| KR | 10-1732876 B1 | 5/2017 |
| WO | WO2006000420 A1 | 1/2006 |

(Continued)

OTHER PUBLICATIONS

Trosko, J.e., et al. in Mutation Research, 480-481, pp. 219-229, 2001.*

(Continued)

*Primary Examiner* — Gollamudi S Kishore
(74) *Attorney, Agent, or Firm* — The PL Law Group, PLLC

(57) ABSTRACT

A method for treatment of cancer selected from the group consisting of metastatic ovarian cancer, endometrial cancer, and breast cancer includes administering a composition comprising a compound represented by Formula 1, a pharmaceutically acceptable salt thereof to a subject in need thereof: The composition can efficiently kill cancer cells present in a spheroid form, thereby being usefully applied as novel medicament for metastatic ovarian cancer, endometrial cancer or breast cancer.

17 Claims, 21 Drawing Sheets

(51) Int. Cl.
 A61P 35/04  (2006.01)
 A61K 33/243  (2019.01)
 A61K 31/165  (2006.01)
 A61K 31/337  (2006.01)
 A61K 31/343  (2006.01)
 A61K 31/475  (2006.01)

(52) U.S. Cl.
 CPC .......... *A61K 31/337* (2013.01); *A61K 31/343* (2013.01); *A61K 31/475* (2013.01); *A61K 33/243* (2019.01); *A61P 35/04* (2018.01); *A23V 2002/00* (2013.01)

(58) Field of Classification Search
 CPC .. A61K 33/243; A61K 31/277; A61K 31/585; A61K 33/34; A61K 45/06; A61K 31/155; A61K 31/496; A23L 33/10; A61P 35/04; A23V 2002/00; A23V 2200/308
 See application file for complete search history.

(56) References Cited

U.S. PATENT DOCUMENTS

| | | | |
|---|---|---|---|
| 2013/0012413 A1* | 1/2013 | DeLouise | C12N 5/0695 506/10 |
| 2013/0296326 A1* | 11/2013 | Pollock | A61K 31/51 514/248 |
| 2015/0072019 A1 | 3/2015 | Kneissel et al. | |
| 2015/0315244 A1* | 11/2015 | ElShamy | A61K 33/243 424/649 |
| 2016/0095842 A1 | 4/2016 | Fritsch et al. | |
| 2017/0100406 A1* | 4/2017 | Jovcheva | A61P 35/02 |

FOREIGN PATENT DOCUMENTS

| | | |
|---|---|---|
| WO | WO 2014/145751 A2 | 9/2014 |
| WO | 2015191996 A1 | 12/2015 |
| WO | WO 2016/091849 A2 | 6/2016 |

OTHER PUBLICATIONS

Twentyman, P.r., et al in Cancer Letters, 9, pp. 225-228, 1980.*
Voskoglou-Nomikos et al, Clinical Cancer Research, vol. 9, pp. 4227-4239, 2003.*
Office action dated Aug. 4, 2020 from Japan Intellectual Property Office in a counterpart Japanese Patent Application No. 2019-537090 (all the cited references are listed in this IDS.).
European Journal of Cancer, 2014, vol. 50, Suppl.5, p. S202, Abstract No. 833.
Fabrice Andre et al."Rationale for targeting fibroblast growth factor receptor signaling in breast cancer" Breast Cancer Research and Treatment, 2015, vol. 150, No. 1, p. 1-8.
"Activity of the Fibroblast Growth Factor Receptor Inhibitors Dovitinib (TKI258) and NVP-BGJ398 in Human Endometrial Cancer Cells" Molecular Cancer Therapeutics, 2013, vol. 12, No. 5, p. 632-642.
International Search Report for PCT/KR2018/000379 dated Apr. 24, 2018.
Masaru Katoh, "FGFR inhibitors: Effects on cancer cells, tumor microenvironment and whole-body homeostasis (Review)", International Journal of Molecular Medicine, vol. 38, pp. 3-15, 2016.
Lucia Nogova et al., "Evaluation of BGJ398, a Fibroblast Growth Factor Receptor 1-3 Kinase Inhibitor, in Patients With Advanced Solid Tumors Harboring Genetic Alterations in Fibroblast Growth Factor Receptors: Results of a Global Phase I, Dose-Escalation and Dose-Expansion Study", Journal of Clinical Oncology, vol. 35, No. 2. Jan. 2017.
Katharina Schmidt et al., "Targeting Fibroblast Growth Factor Receptor (FGFR) with BGJ398 in a Gastric Cancer Model", Anti-cancer Research, vol. 35, pp. 6655-6666, 2015.
Vito Guagnano et al., "FGFR Genetic Alterations Predict for Sensitivity to NVP-BGJ398, a Selective Pan-FGFR Inhibitor", Cancer Discovery, 2012.
Michele Zanoni et al., "3D tumor spheroid models for in vitro therapeutic screening: a systematic approach to enhance the biological relevance of data obtained". Scientific Reports, 2016.
The extended European Search Report For EP18736528.3 dated Sep. 15, 2020 from European patent office in a counterpart European patent application.
Xue B. Holdman et al. "Upregulation of EGFR signaling is correlated with tumor stroma remodeling and tumor recurrence in FGFR1-driven breast cancer" vol. 17, No. 1, 2015.
Sara A. Byron et al. "Fibroblast Growth Factor Receptor Inhibition Synergizes With Paclitaxel and Doxorubicin in Endometrial Cancer Cells" Int J Gynecol Cancer, vol. 22, No. 9, 2012, pp. 1517-1526.
Fiona H. Tan et al. "The role of STAT3 signaling in mediating tumor resistance to cancer therapy" Current Drug Targets, vol. 15, No. 14, 2014, pp. 1341-1353.
RC Turkington et al. "Fibroblast growth factor receptor 4 (FGFR4): a targetable regulator of drug resistance in colorectal cancer" Cell Death and Disease, vol. 5, No. 2, 2014.
Zhiqiang Han et al. "A Potent Oncolytic Adenovirus Selectively Blocks the STAT3 Signaling Pathway and Potentiates Cisplatin Antitumor Activity in Ovarian Cancer" Human Gene Therapy 23:32-45.
Hiwa Jun Cha et al. "Selective FGFR inhibitor BGJ398 inhibits phosphorylation of AKT and STAT3 and induces cytotoxicity in sphere-cultured ovarian cancer cells" International Journal of Oncology vol. 50, pp. 1279-1288, 2017.
Se Hyun Kim et al. "BGJ398, A Pan-FGFR Inhibitor, Overcomes Paclitaxel Resistance in Urothelial Carcinoma with FGFR1 Overexpression" International Journal of Molecular Sciences, vol. 19, 2018, p. 3164.
Office action dated Jul. 27, 2022 from China Patent Office in a counterpart China Patent Application No. 201880016255.3 (all the cited references are listed in this IDS.) (English translation is also submitted herewith.).
Li Ning et al., "Taxol resistance in ovarian cancer and its management", Oncology Process, vol. 6(1), Jan. 2008 (English Translation of Abstract is included in the first page.).

* cited by examiner

FIG. 3
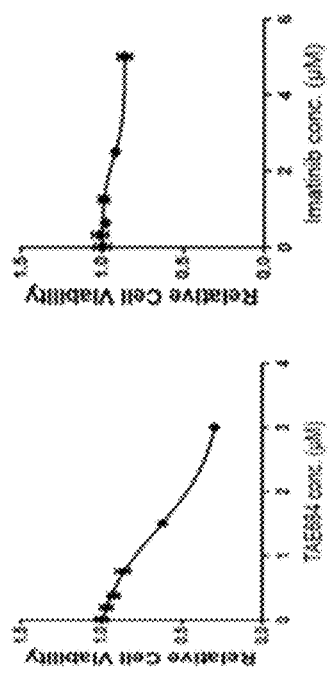
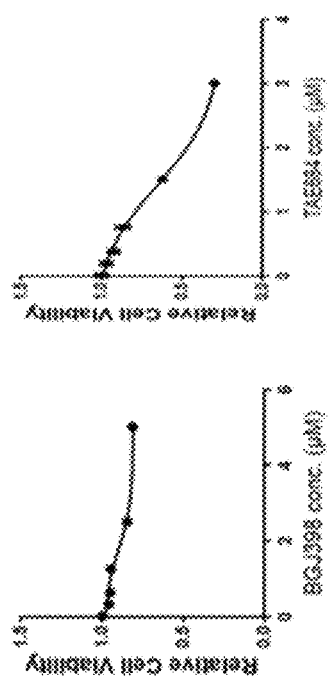
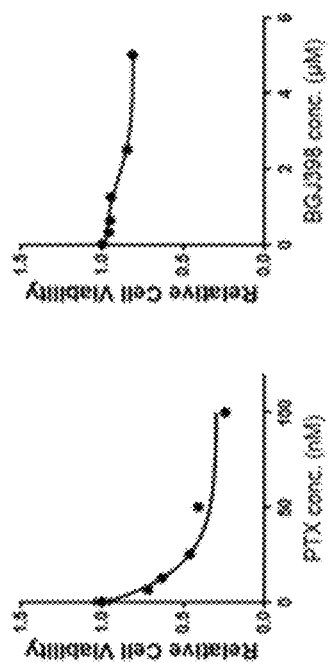
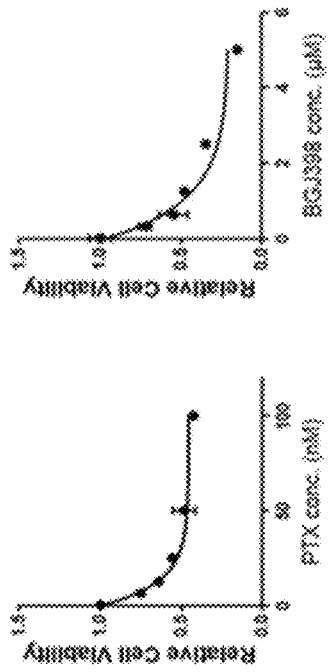

FIG. 7
A
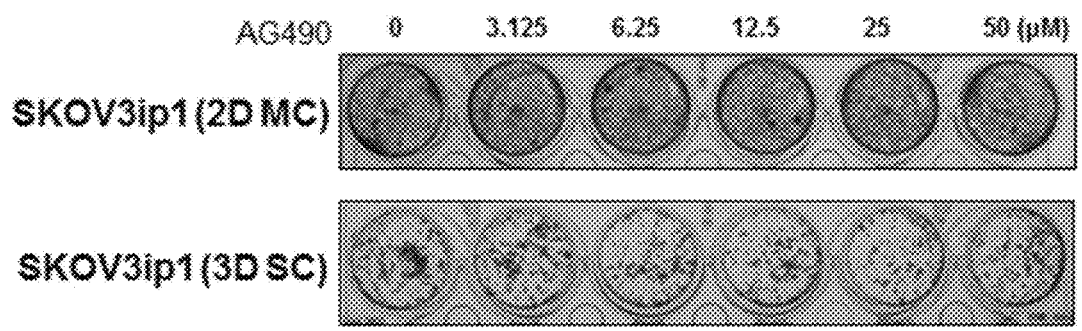
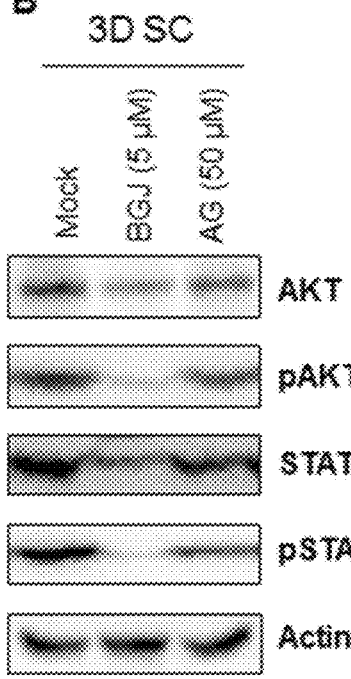

FIG. 8
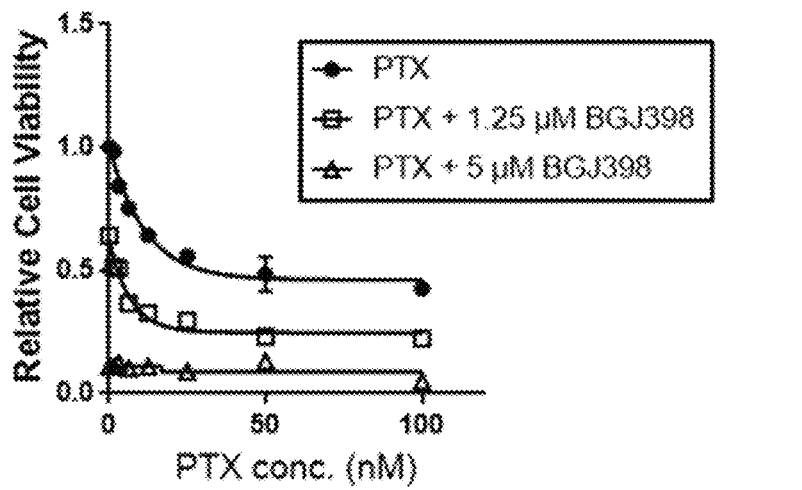
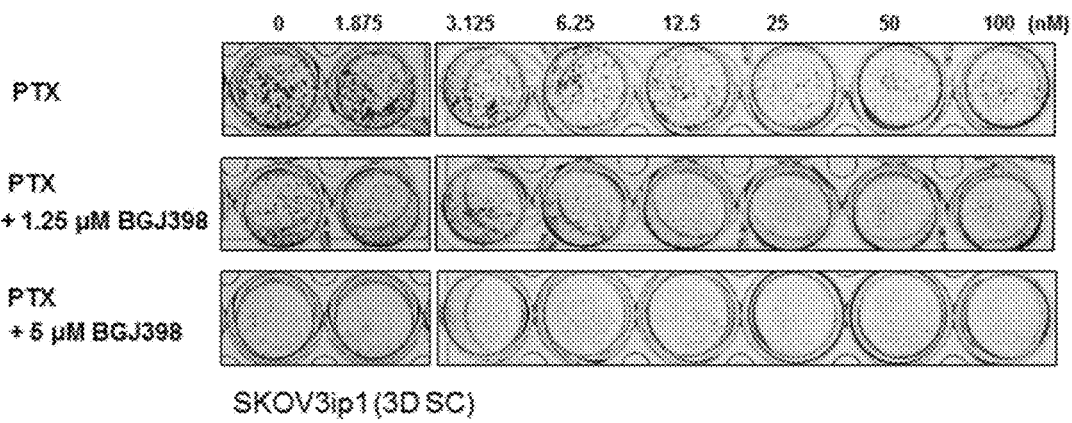
SKOV3ip1 (3D SC)
FIG. 9
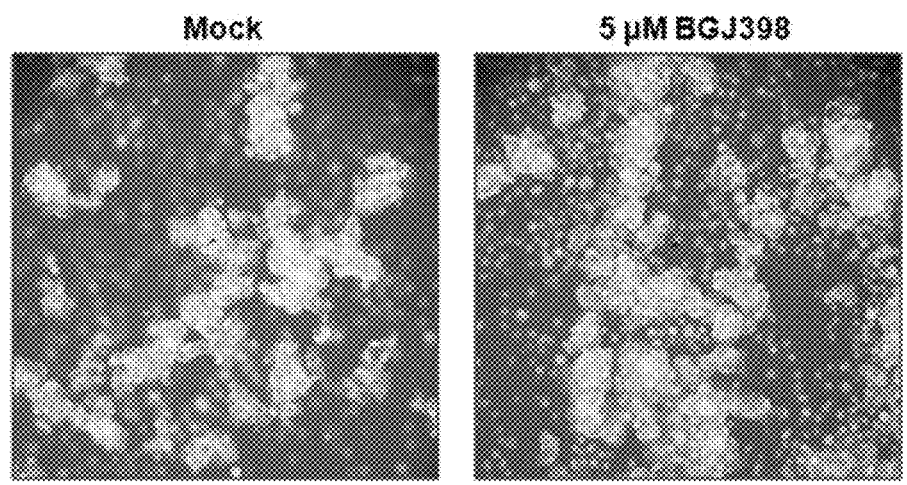
HEC1B endometrial cancer cell line (sphere culture)

FIG. 10
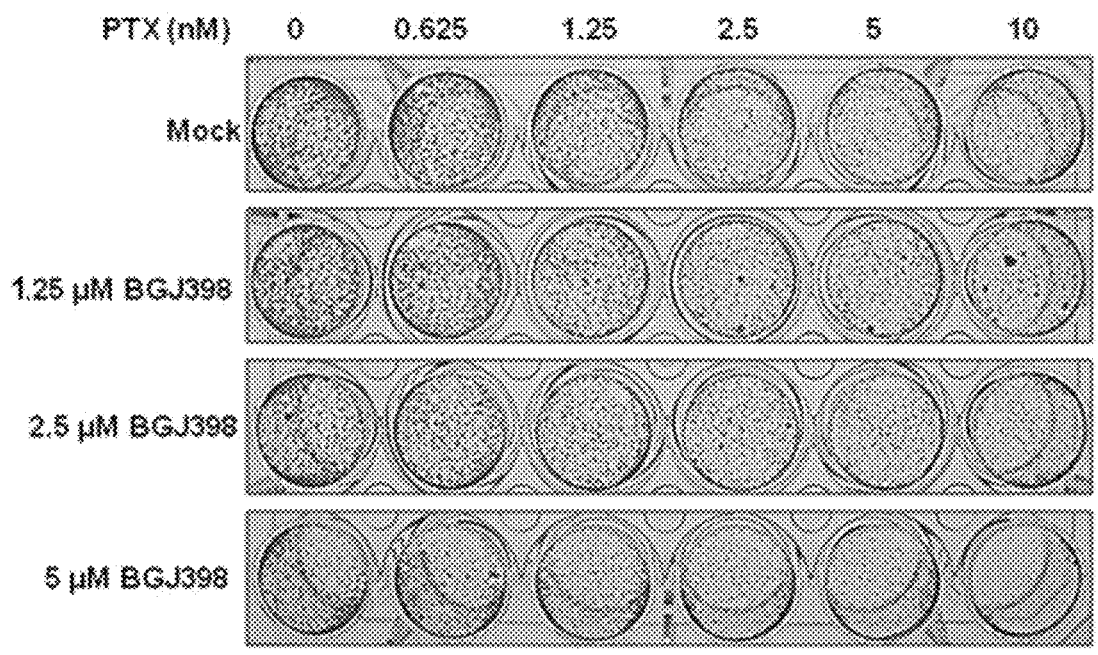
HEC1B endometrial cancer cell line
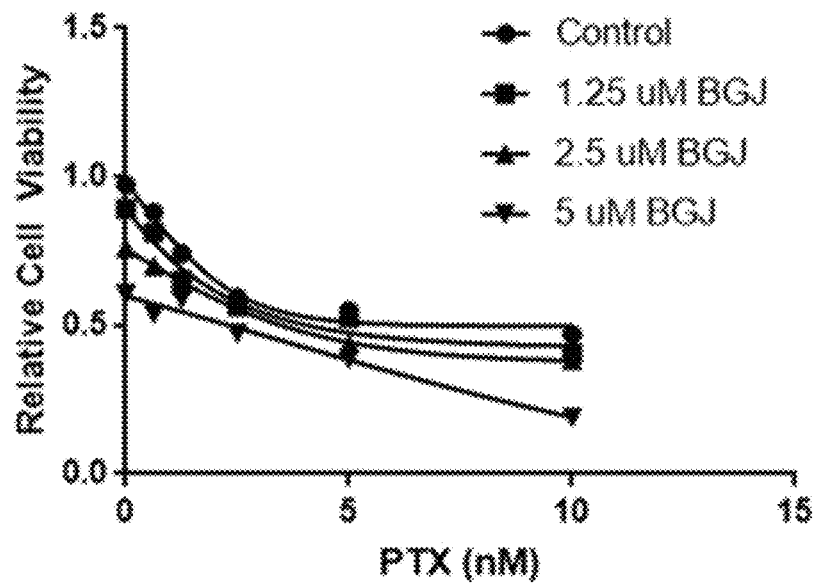

HEC1B endometrial cancer cell line

Hs578T breast cancer cell line (sphere culture)

Hs578T breast cancer cell line

COMPOSITION FOR PREVENTING OR TREATING METASTATIC OVARIAN CANCER, ENDOMETRIAL CANCER OR BREAST CANCER

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2018/000379, filed Jan. 8, 2018, which claims priority to the benefit of Korean Patent Application No. 10-2017-0002180 filed on Jan. 6, 2017 and 10-2018-0002491 filed on Jan. 8, 2018 in the Korean Intellectual Property Office, the entire contents of which are incorporated herein by reference.

TECHNICAL FIELD

The present invention relates to a pharmaceutical composition or a health functional supplement for preventing or treating metastatic ovarian cancer, endometrial cancer or breast cancer.

BACKGROUND ART

Ovarian cancer is a cancer having the highest mortality among all gynecologic cancers, and with recently westernized lifestyle and increased aging population, an incidence of the ovarian cancer has steadily increased. In a case of the ovarian cancer, progressive ovarian cancer in at least stage III is firstly discovered in more than 70% of patients because obvious symptoms do not appear in early days, and it has been reported that recurrence and metastasis occur in 2 years after first treatment in more than 75% of patients.

Methods for treatment of ovarian cancer are determined in accordance with types and stages of the cancer and may include surgery, chemotherapy, etc. However, such methods are not significantly effective in treating metastatic cancer due to recurrence. This is because cancer metastasis involves induction of neovascularization ('angiogenesis') and cell migration, which are different from the cancer itself in terms of status. For example, in order to prevent the metastasis of cancer, it is necessary to inhibit induction of angiogenesis as well as cell migration, and therefore, anti-metastatic effects are clearly distinguishable from anticancer effects.

The ovarian cancer often progresses without exhibiting specific symptoms and is difficult to be early detected. Further, in a case in which the ovarian cancer is confirmed, most cases of the cancer are in advanced stages and often show peritoneal metastasis. In addition, since the ovaries freely move within the pelvis, cancer cells may infiltrate into surrounding tissues, or as compared to other cancers, the ovarian cancer has a characteristic of faster metastasis. Due to these effects, about 70 to 75% or more of all ovarian cancer patients have been diagnosed with at least stage III advanced ovarian cancer. In particular, it is known that terminal-stage ovarian cancer cells exist in a spherical shape such as spherical mass of cancer cells in ascetic fluid, and due to the above-described specific properties of the ovarian cancer cells, cancer cell death ("apoptosis") is not effectively induced even though the cancer cells are treated with a typical anticancer drug having effects on other cancers. Further, it was reported that the ovarian cancer cells are resistant to different anticancer drugs.

Further, the problem such as anticancer drug resistance also appears in endometrial cancer, breast cancer, etc.

Accordingly, there is a need for development of novel anticancer drugs, in particular: a novel anticancer drug which desirably exhibits anticancer effects on specific metastatic forms of ovarian cancer thus to efficiently perform apoptosis of metastatic ovarian cancer cells; a novel anticancer drug which exhibits excellent efficacy on endometrial cancer, breast cancer, etc.; and a novel anticancer drug which overcomes resistance of the cancer cells having the resistance to the conventional anticancer drugs.

SUMMARY

Accordingly, an object of the present invention is to provide a novel anticancer drug effective for extinction of metastatic ovarian cancer, which is floating in ascetic fluid and presents in a spherical form, as well as endometrial cancer and breast cancer.

Another object of the present invention is to provide an anticancer adjuvant capable of blocking anticancer drug-resistance of cancer cells.

Another object of the present invention is to provide a health functional supplement that can exhibit excellent health function for metastatic ovarian cancer, endometrial cancer and breast cancer.

Another object of the present invention is to provide a method for treatment of metastatic ovarian cancer, endometrial cancer and breast cancer.

Further, another object of the present invention is to provide use of a specific compound in manufacturing medicament for treatment of metastatic ovarian cancer, endometrial cancer and breast cancer.

1. A pharmaceutical composition for preventing or treating metastatic ovarian cancer, endometrial cancer or breast cancer, including a compound represented by Formula 1 below or a pharmaceutically acceptable salt thereof:

[Formula 1]

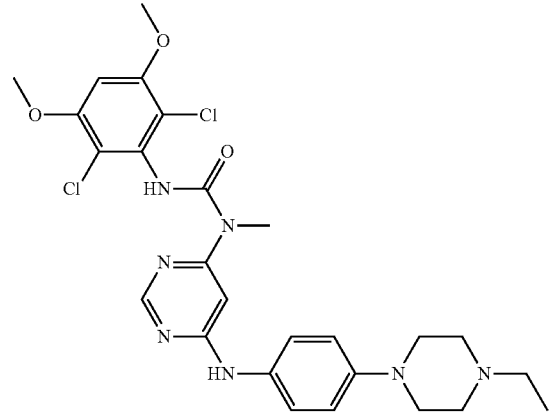

2. The pharmaceutical composition according to above 1, wherein the metastatic ovarian cancer, endometrial cancer or breast cancer includes cancer cells, a part of which is in a spheroid form.

3. The pharmaceutical composition according to above 1, wherein the compound represented by Formula 1 or the pharmaceutically acceptable salt thereof degrades the spheroid form of the cancer cell.

4. The pharmaceutical composition according to above 1, wherein the metastatic ovarian cancer is stage III or stage IV ovarian cancer.

5. The pharmaceutical composition according to above 1, wherein the metastatic ovarian cancer, endometrial cancer or breast cancer is a cancer resistant to a chemical anticancer agent.

6. The pharmaceutical composition according to above 1, wherein the pharmaceutical composition is administered in combination with a chemical anticancer agent.

7. The pharmaceutical composition according to above 6, wherein the chemical anticancer agent is an antimitotic agent, an alkylating agent or cisplatin.

8. The pharmaceutical composition according to above 6, wherein the chemical anticancer agent includes paclitaxel.

9. The pharmaceutical composition according to above 1, wherein the pharmaceutical composition further includes a chemical anticancer agent such as an antimitotic agent or an alkylating agent.

10. The pharmaceutical composition according to above 1, wherein the pharmaceutical composition further includes paclitaxel.

11. An anticancer adjuvant for metastatic ovarian cancer, endometrial cancer or breast cancer, including a compound represented by Formula 1 below or a food-scientifically acceptable salt thereof:

[Formula 1]

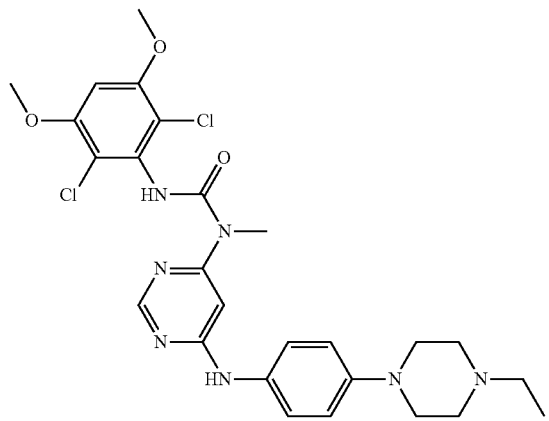

12. The anticancer adjuvant according to above 11, wherein the metastatic ovarian cancer, endometrial cancer or breast cancer is a cancer resistant to a chemical anticancer agent.

13. The anticancer adjuvant according to above 11, wherein the anticancer adjuvant is administered in combination with a chemical anticancer agent.

14. The anticancer adjuvant according to above 13, wherein the chemical anticancer agent is an antimitotic agent or an alkylating agent.

15. The anticancer adjuvant according to above 13, wherein the chemical anticancer agent includes paclitaxel.

16. A health functional supplement for preventing or improving metastatic ovarian cancer, endometrial cancer or breast cancer, including a compound represented by Formula 1 below or a food-scientifically acceptable salt thereof:

[Formula 1]

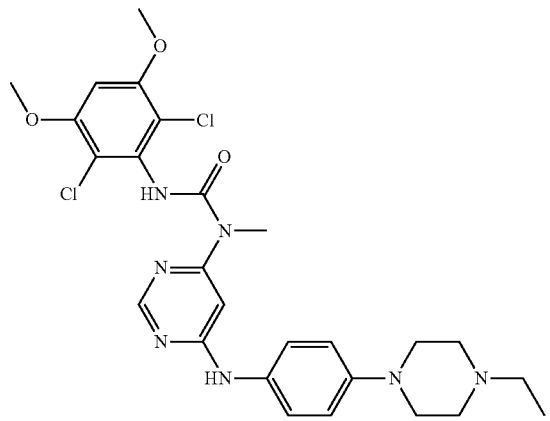

17. The health functional supplement according to above 16, wherein the metastatic ovarian cancer, endometrial cancer or breast cancer includes cancer cells, a part of which is in a spheroid form.

18. The health functional supplement according to above 16, wherein the metastatic ovarian cancer is stage III or stage IV ovarian cancer.

19. The health functional supplement according to above 16, wherein the compound represented by Formula 1 or the food-scientifically acceptable salt thereof degrades the spheroid form of the cancer cell.

20. A method for treatment of metastatic ovarian cancer, endometrial cancer or breast cancer, including administering a compound represented by Formula 1 below or a pharmaceutically acceptable salt thereof to an object:

[Formula 1]

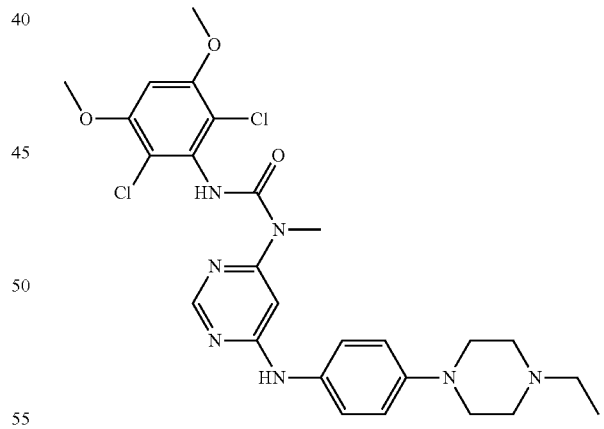

21. The method according to above 20, wherein the metastatic ovarian cancer, endometrial cancer or breast cancer includes cancer cells, a part of which is in a spheroid form.

22. The method according to above 20, wherein the metastatic ovarian cancer is stage III or stage IV ovarian cancer.

23. The method according to above 20, wherein the compound represented by Formula 1 or the pharmaceutically acceptable salt thereof degrades the spheroid form of the cancer cell.

24. The method according to above 20, wherein the metastatic ovarian cancer, endometrial cancer or breast cancer is a cancer resistant to a chemical anticancer agent.

25. The method according to above 20, wherein the compound represented by Formula 1 or the pharmaceutically acceptable salt thereof is administered in combination with a chemical anticancer agent.

26. The method according to above 25, wherein chemical anticancer agent-resistance of the cancer of the object is identified before co-administration of the chemical anticancer agent, and then, the chemical anticancer agent is co-administered to the object who was identified to acquire the chemical anticancer agent-resistance.

27. The method according to above 25, wherein the chemical anticancer agent is an antimitotic agent or an alkylating agent.

28. The method according to above 25, wherein the chemical anticancer agent includes paclitaxel.

29. Use of a compound represented by Formula 1 below or a pharmaceutically acceptable salt thereof in manufacturing medicament for preventing or treating metastatic ovarian cancer, endometrial cancer or breast cancer:

[Formula 1]

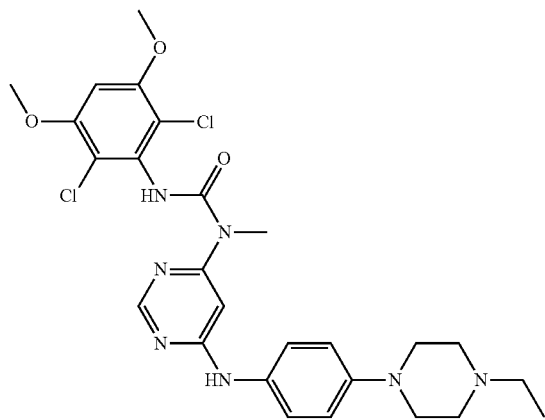

30. The use according to above 29, wherein the metastatic ovarian cancer, endometrial cancer or breast cancer includes cancer cells, a part of which is in a spheroid form.

31. The use according to above 29, wherein the metastatic ovarian cancer is stage III or stage IV ovarian cancer.

32. The use according to above 29, wherein the compound represented by Formula 1 or the pharmaceutically acceptable salt thereof degrades the spheroid form of the cancer cell.

33. The use according to above 29, wherein the metastatic ovarian cancer, endometrial cancer or breast cancer is a cancer resistant to a chemical anticancer agent.

The pharmaceutical composition of the present invention can efficiently kill cancer cells present in a spheroid form, thereby being usefully applied as novel medicament for metastatic ovarian cancer, endometrial cancer or breast cancer.

BRIEF DESCRIPTION OF THE DRAWINGS

FIG. 3 is diagrams illustrating results of identifying cell viability when cultured SKOV3ip1 ovarian cancer cells were treated with paclitaxel (PTX), BGJ398, TAE684 and imatinib, respectively, at different concentrations, after (A) 2-dimensional monolayer culture (2D MC) and (B) 3-dimensional sphere culture (3D SC).

FIG. 7 is diagrams illustrating (A) results of identifying cell apoptotic effects, obtained from treatment of cultured SKOV3ip1 ovarian cancer cells with AG490 at different concentrations after 2-dimensional monolayer culture (2D MC) and 3-dimensional sphere culture (3D SC); and (B) results of identifying a change in phosphorylation degrees of AKT and STAT3, when cultured SKOV3ip1 ovarian cancer cells were treated with BGJ398 (BGJ) and AG490 (AG), respectively, after 3-dimensional sphere culture (3D SC).

FIG. 8 is diagrams illustrating results of identifying cell viability, when cultured SKOV3ip1 ovarian cancer cells were treated with paclitaxel (PTX) alone and in combination with BGJ398, respectively, after 3-dimensional sphere culture (3D SC).

FIG. 9 is diagrams illustrating results of observation of the shape of cells through a microscope, when HEC1B endometrial cancer cell line was treated with BGJ398, after 3-dimensional sphere culture (3D SC).

FIG. 10 is diagrams illustrating results of identifying cell apoptotic effects through crystal violet staining and graphs, when HEC1B endometrial cancer cell line was treated with an anticancer drug paclitaxel at different concentrations in combination with BGJ398.

DETAILED DESCRIPTION

Figure 1:
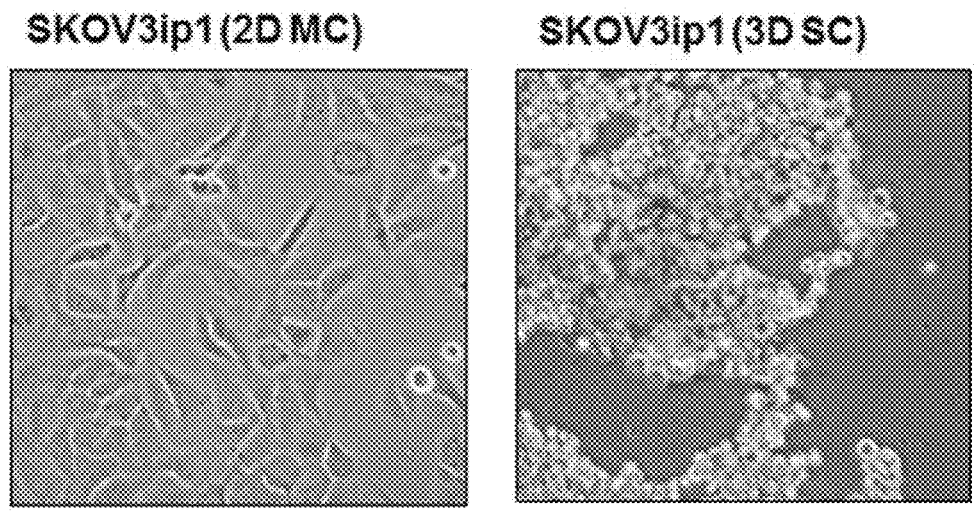
FIG. 1 is diagrams illustrating results of observation of shape of cultured SKOV3ip1 ovarian cancer cells under a microscope after 2-dimensional monolayer culture (2D MC) and 3-dimensional sphere culture (3D SC).

The present invention relates to a pharmaceutical composition for preventing or treating metastatic ovarian cancer, endometrial cancer or breast cancer, which includes a compound represented by Formula 1 below or a pharmaceutically acceptable salt thereof:

[Formula 1]

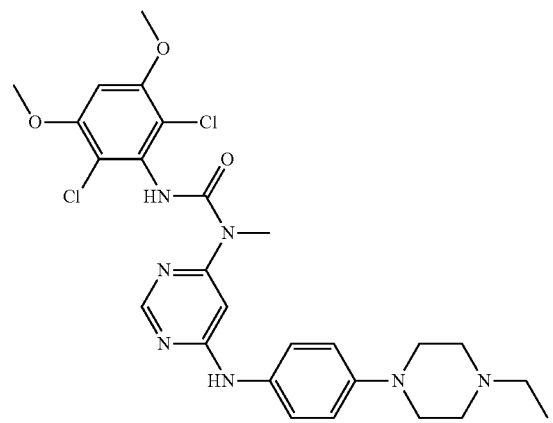

The compound represented by Formula 1 is BGJ398 (CAS Number: 872511-34-7) as a FGFR inhibitor and may target all of FGFR 1 to 4. This compound has a chemical formula of $C_{26}H_{31}Cl_2N_7O_3$ and a chemical name of 3-(2,6-dichloro-3,5-dimethoxyphenyl)-1-[6-[4-(4-ethylpiperazin-1yl)anilino]pyrimidin-4-yl]-1-methylurea.

With respect to the pharmaceutically acceptable salt of the compound represented by Formula 1 (often referred to as 'compound of Formula 1') according to the present invention, types of the salt may include a variety of salts having biological effectiveness and properties of the compound without particular limitation thereof. For example, pharmaceutically acceptable acid addition salts may include, for example, salts of inorganic acids and organic acids such as acetate, aspartate, benzoate, besylate, bicarbonate, carbonate, bisulfate, sulfate, camphor sulfonate, chloride, hydrochloride, chlorotheophylline rotate, citrate, ethane disulfonate, fumarate oxalate, palmitate, pamoate, phosphate, hydrogen phosphate, dihydrogen phosphate, propionate, stearate, succinate, salicylate, tartrate, tosylate and trifluoroacetate salts and the like. The inorganic acids, salts of which can be derived, may include, for example, hydrochloric acid, hydrobromic acid, sulfuric acid, nitric acid, phosphoric acid and the like. Preferred examples of BGJ398 or a pharmaceutically acceptable salt thereof in the present invention may be phosphoric acid salts.

As used herein, the "metastatic ovarian cancer" refers to ovarian cancer wherein cancer cells have spread to the abdominal cavity, unlike primary ovarian cancer derived from and attached to ovarian surface epithelium. The terminal-stage metastatic ovarian cancer cells are characterized by being present in a sphere (spheroid) form in ascetic fluid.

With respect to definition of the stages of ovarian cancer in relation to metastasis degree of the ovarian cancer, the ovarian cancer having spread to the abdomen is defined as "Stage III ovarian cancer", wherein the cancer has spread to the liver, large intestine, small intestine, bladder, abdominal cavity, lymph nodes inside the peritoneum, etc. "Stage IV ovarian cancer" means that the cancer has metastasized beyond the abdomen and spread to other organs such as the lung, bone, neck, lymph nodes around the brain, and may be called distant metastasis.

As used herein, the "endometrial cancer" means the cancer occurred in the endometrium covering the uterine area, and with respect to definition of the stage of the endometrial cancer in relation to the metastasis degree, "stage III endometrial cancer" is defined as a state that did not invade the bladder or rectum without metastasis outside the pelvis although the cancer has spread to tissues around the uterine, and means the cancer having metastasized to serosa, ovaries, fallopian tubes, vagina, pelvic wall, aortic lymph nodes, etc. Meanwhile, "stage IV endometrial cancer" is defined as the cancer that invaded the bladder or rectum or metastasized out of the pelvis.

As used herein, the "breast cancer" means the cancer occurred in the breast, and with respect to definition of the stage of the breast cancer in relation to the metastasis degree, "stage III breast cancer" is defined as a state wherein the cancer has spread to lymph nodes in the underarm and the lymph nodes were thoroughly agglomerated or fixed to surrounding tissues, or a state that the cancer has spread to lymph nodes above or below the clavicle. Meanwhile, "stage IV breast cancer" is defined as a distant metastasis condition that the cancer has spread to other organs such as the bone, lung, liver or brain.

The compound represented by Formula 1 or the pharmaceutically acceptable salt thereof according to the present invention may degrade the spheroid form of cancer cells.

As used herein, the spheroid form of cancer cells means a spherical mass formed of cancer cells, that is, a sphere which is a structure to form 3D aggregates. As used herein, the term 'spheroid' may be interchangeably used with a sphere, spherical body, globoid, etc., in addition, include a meaning of ellipsoids, balls, etc. without particular limitation. The present inventors have found that, when cancer cells are subjected to 3D culture to induce a metastatic cancer-like state, the cancer cells lead to a spheroid form and become a floating state. In contrast to treatment using the conventional anticancer drug, it was found that the cancer cells having a spheroid aggregate form do not maintain a normal aggregate state by treatment using the compound of Formula 1 but exhibit degradation of the spheroid form. Accordingly, the pharmaceutical composition of the present invention may be a pharmaceutical composition having therapeutic efficacy on the cancer forming a spheroid shape.

The compound of Formula 1 or the pharmaceutically acceptable salt thereof may inhibit maintaining the spheroid shape in 3D cultured ovarian cancer cells that can reflect metastatic ovarian cancer cells involving micro-environments wherein the cancer cells float in ascetic fluid and may prevent a cell survival signaling pathway, thereby exhibiting anticancer effects specific to the metastatic ovarian cancer rather than typical attachable primary ovarian cancer. Therefore, the pharmaceutical composition of the present invention may be used for preventing or treating, for example, stage III or IV ovarian cancer.

Further, the compound of Formula 1 or the pharmaceutically acceptable salt thereof may inhibit phosphorylation of AKT and STAT3, which in turn can prevent or treat the metastatic ovarian cancer characterized by increased phosphorylation of fibroblast growth factor receptor (FGFR).

Further, according to the present invention, it was found that cell survival signals rather than cell proliferation have increased in the metastatic ovarian cancer cells embodied through 3D sphere culture. In particular, it was demonstrated that the cell survival signaling molecules, that is, AKT and STAT3 show significantly high phosphorylation. Further, such an increase in phosphorylation is not identified in the adherent-cultured ovarian cancer cells observed through typical 2D single culture, and therefore, it was determined that AKT and STAT3 signaling mechanisms are used for cell survival of the metastatic ovarian cancer. Such increased AKT and STAT3 phosphorylation and FGFR phosphorylation are reduced by treatment using the compound of Formula 1, thereby exhibiting cell apoptotic effects on the metastatic cancer cells.

Accordingly, the present invention may provide a pharmaceutical composition for preventing or treating ovarian cancer, characterized in that the compound of Formula 1 or the pharmaceutically acceptable salt thereof can inhibit AKT and STAT3 phosphorylation. In particular, there is provided a pharmaceutical composition for preventing or treating ovarian cancer wherein the metastatic ovarian cancer shows increased phosphorylation of fibroblast growth factor receptor (FGFR).

According to the present invention, the metastatic ovarian cancer, endometrial cancer or breast cancer may be a cancer resistant to chemical anticancer agents (sometimes, "a chemo-resistant cancer"). Such resistance may be reduced by treatment using the compound of Formula 1 or the pharmaceutically acceptable salt thereof.

The chemical anticancer agent may be a chemical anticancer agent as being widely used in the art, and may include, for example, nitrogen mustard, imatinib, oxaliplatin, rituximab, erlotinip, trastuzumab, gefitinib, bortezomib, sunitinib, carboplatin, sorafenip, bevacisumab, cetuximab, viscumalbum, asparaginase, tretinoin, hydroxycarbamide, dasatinib, estramustine, gemtuzumab ozogamicin, ibritumomab tiuxetan, heptaplatin, methyl aminolevulinic acid, amsacrine, alemtuzumab, procarbazine, alprostadil, holmium nitrate chitosan, gemcitabine, doxifluridine, pemetrexed, tegafru, capecitabine, gimeracin, oteracil, azacitidine, cytarabine, fludarabine, enocitabine, decitabine, mercaptopurine, thioguanine, cladribine, carmofur, raltitrexed, docetaxel, paclitaxel, belotecan, topotecan, vinorelbine, etoposside, vincristine, vinblastine, colchicines, griseofulvin, teniposide, idarubicin, epirubicin, mitoxantrone, mitomycin, bleomycin, daunorubicin, dactinomycin, pirarubicin, aclarubicin, pepiomycin, temozolomide, busulfan, ifosfamide, cyclophosphamide, melphalan, altretamine, dacabazine, thiotepa, nimustine, chlorambucil, mitolactol, taxotere, gleevec, taxol, herceptin, tarceva, avastin, zoladex, adriamycin, irinotecan, 10058-F4, cisplatin, cyclohosphamide, nitrosourea-based anticancer drugs, methotrexate, doxorubicine and the like.

In particular, the chemical anticancer agent may include an antimitotic agent or an alkylating agent. The antimitotic agent may include, for example, paclitaxel, docetaxel, vinblastin, vincristine, vinorelbine, colchicine and griseofulvin. Meanwhile, the alkylating agent may include, for example, cysplatin. More particularly, paclitaxel may be used.

As used herein, "resistance" means that no effective level of cancer cell apoptosis is expressed as expected when the chemical anticancer agent is treated. If at least a part of the cancer cells is in a spheroid form, the cancer cells may have higher resistance to the chemical anticancer agent than the attachable cancer cells without the spheroid form. As described above, the compound of Formula 1 or the pharmaceutically acceptable salt thereof may degrade the spheroid form of cancer cells, thereby exhibiting superior efficacy to even such chemical anticancer agent-resistant cancers as described above. If necessary, the pharmaceutical composition of the present invention may be administered in combination with the chemical anticancer agents. As described above, the pharmaceutical composition of the present invention has excellent efficacy to even the chemical anticancer agent-resistant cancers, and therefore, may be used in combination with the chemical anticancer agents thus to maximize efficacy thereof. The chemical anticancer agents used in combination with the present composition may be, for example, at least one among the above-described chemical anticancer agents.

A procedure of such combined administration is not particularly limited, and the inventive composition may be simultaneously or sequentially administered with the chemical anticancer agent.

The inventive composition may include any pharmaceutically acceptable carrier. Such acceptable carrier included in the pharmaceutical composition of the present invention is any one commonly used at the time of preparation and may include, for example, lactose, dextrose, sucrose, sorbitol, mannitol, starches, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, saline solution, phosphate buffered saline (PBS) or a medium, without limitation thereto.

The pharmaceutical composition of the present invention may further include lubricants, humectants, sweeteners, flavoring agents, emulsifiers, suspending agents, preservatives, etc. in addition to the above components.

The pharmaceutical composition of the present invention may be administered orally or parenterally, and preferably, can be administered orally.

A suitable dose of the pharmaceutical composition according to the invention may vary depending on different factors such as a formulation method, administration procedure, age, body weight, sex or condition, daily food, administration time, administration route, excretion rate and response sensitivity of a patient, and a variety of prescriptions may be provided.

Further, the invention also relates to an anticancer adjuvant for metastatic ovarian cancer, endometrial cancer or breast cancer, which includes the compound represented by Formula 1 or the pharmaceutically acceptable salt thereof.

As used herein, the "anticancer adjuvant" refers to a substance used in combination with the chemical anticancer agent in order to assist/improve therapeutic efficacy of the anticancer agent. As described above, the compound of Formula 1 or the pharmaceutically acceptable salt thereof may block anticancer agent resistance/tolerance of cancer cells, and therefore, be used in combination with a chemical anticancer agent to maximize the anticancer efficacy.

The chemical anticancer agent used in combination may be, for example, at least one among the above-described chemical anticancer agents. Further, the administration procedure in the combined administration is not particularly limited. That is, the inventive compound may be simultaneously or sequentially administered with the chemical anticancer agent.

Further, the present invention relates to a health functional supplement for preventing or improving metastatic ovarian cancer, endometrial cancer or breast cancer, which includes the compound represented by Formula 1 or the pharmaceutically acceptable salt thereof.

As used herein, the health functional supplement means food with biological control performance such as prevention or improvement of diseases, bio-defense, immunization, recovery of illness, aging inhibition, etc., which should be harmless to the human body when taken for a long term.

The metastatic ovarian cancer, endometrial cancer or breast cancer, to which the health functional supplement of the present invention can be applied, may be the same as described above.

The compound represented by Formula 1 or the pharmaceutically acceptable salt thereof may be directly formulated as a health functional supplement or may be added to typical foods.

When adding to the typical foods, the health functional supplement may be directly added or used in conjunction with other foods or food ingredients. The inventive supplement may be suitably used in any conventional manner. An amount of active ingredient to be mixed may be properly determined according to purposes of use (prevention, heath care or therapeutic treatment). In general, the compound of Formula 1 or the pharmaceutically acceptable salt thereof in manufacturing food or beverage is added in an amount of 15% by weight ('wt. %') or less or, preferably, 10 wt. % or less to a raw material. However, in a case of long-term intake for purposes of health and hygiene or for regulating health condition, the added amount may be less than the above range. Further, since there is no problem in an aspect of safety, the active ingredient may be used in an amount more than the above range.

Types of the food are not particularly limited. The foods to which the inventive material can be added may include, for example, meats, sausages, breads, chocolates, candies, snacks, cookies, pizza, ramen or other noodles, gums, dairy products including ice cream, various soups, beverages, tea, drinks, and alcoholic drinks and vitamin complex, etc., and substantially include all types of health food in general definition.

The composition for health beverages according to the present invention may include additional components such as various flavors or natural carbohydrates, like as conventional beverages. The above-described natural carbohydrates may include: monosaccharide such as glucose, fructose, etc.; disaccharides such as maltose, sucrose, etc.; natural sweeteners such as dextrin, cyclodextrin, etc.; or synthetic sweeteners such as saccharin, aspartame, etc. A content of the natural carbohydrates may range from about 0.01 to 10 g, preferably, about 0.01 to 0.1 g to 100 ml of the inventive composition.

In addition, the health functional supplement of the present invention may further include various nutrients, vitamins, electrolytes, flavoring agents, coloring agents, pectic acid and its salts, alginic acid and its salts, organic acid, protective colloidal thickeners, pH adjusting agents, stabilizers, preservatives, glycerin, alcohol and carbonating agents used in soft drinks.

In addition, the health functional supplement of the present invention may further contain fruit flesh for production of natural fruit juices, fruit juice beverages and vegetable beverages. The above components may be used independently or in combination with two or more thereof. A content of the additive described above is not critical but may be generally selected in a range of 0.01 to 0.1 wt. parts based on 100 wt. parts of the health functional supplement of the present invention.

Further, the present invention relates to a method for treatment of metastatic ovarian cancer, endometrial cancer or breast cancer, which includes administering the compound represented by Formula 1 or the pharmaceutically acceptable salt thereof of the present invention to a subject.

The subject refers to a patient who requires cancer treatment, and preferably, includes mammals including human being. The patient may include all of patients under cancer treatment, patients having received cancer treatment and patients who need cancer treatment, and may further include patients who have received surgical procedure to remove (extract) the cancer for the purpose of cancer treatment.

The metastatic ovarian cancer, endometrial cancer or breast cancer to which the inventive treatment method can be applied may be the same as described above.

The treatment method of the present invention may include administration of the compound represented by Formula 1 or the pharmaceutically acceptable salt thereof in combination with a chemical anticancer agent.

The cancer to which the inventive treatment method is applied may include chemical anticancer agent-resistant cancers (often called "a chemo-resistant cancer"). Before deciding co-administration of the chemical anticancer agent, whether the cancer in the subject is a chemo-resistant cancer or not should be determined. Then, if the cancer is identified as the chemo-resistant cancer, the compound of Formula 1 or the pharmaceutically acceptable salt thereof may be administered in combination with the chemical anticancer agent, without being particularly limited thereto.

The chemical anticancer agent useable in combination may be, for example, at least one among the above-described chemical anticancer agents. Further, the administration procedure in combined administration is not particularly limited, and the inventive compound or pharmaceutically acceptable salt thereof may be simultaneously or sequentially administered with the chemical anticancer agent.

The compound of Formula 1 or the pharmaceutically acceptable salt thereof may be administered as a composition including the active ingredient together with other components, as described above, which may be administered orally or parenterally, and preferably, administered orally.

A proper dosage may be differently prescribed on the basis of various factors such as a pharmaceutical formulation method, administration procedure, age, body weight, sex or condition, daily food, administration time, administration route, excretion rate, response sensitivity of a patient or the like.

Further, the present invention relates to use of the compound represented by Formula 1 or the pharmaceutically acceptable salt thereof in manufacturing medicament for preventing or treating metastatic ovarian cancer, endometrial cancer or breast cancer.

The metastatic ovarian cancer, endometrial cancer or breast cancer in the use of the present invention may be the same as described above.

As described above, the compound of Formula 1 or the pharmaceutically acceptable salt thereof may exhibit superior therapeutic efficacy to the metastatic ovarian cancer, endometrial cancer or breast cancer, thereby being used in manufacturing medicament for preventing or treating the above cancers.

The medicament according to the present invention may include the above-described pharmaceutical composition.

Hereinafter, the present invention will be described in detail by way of examples. However, the following examples are only proposed for illustrative purpose of the present invention and are not intended to restrict the content of the present invention.

All statistical analyses were performed by three (3) independent experiments. Differences between individual groups were estimated by a student's t-test, wherein $p \leq \leq 0.05$ is considered to be significant. All graphs are expressed as mean and standard deviation.

Example 1. Comparison of SKOV3ip1 Ovarian Cancer Cells in 2D Monolayer Culture Model and 3D Sphere Culture Model 1.1 2D Monolayer Culture and 3D Sphere Culture Method SKOV3ip1 cell line including SKOV3 ovarian cancer cell line as metrocyte was used as the ovarian cancer cell line. SKOV3 cell line has features of metastatic ovarian cancer isolated from ascetic fluid in an ovary and is a cell line separated after primary proliferation in the abdominal cavity of a nude mouse used as an animal model, which has very high abdominal metastasis ability. SKOV3ip1 cell line was offered by Professor Sood AK (University of Texas MD Anderson Cancer Center, USA) and then used in experiments.

2D monolayer culture was implemented in the following manner: cells were cultured at 37° C., 5% CO humidified atmosphere using RPMI 1640 medium (Corning, NY, USA) supplemented with 10% fetal bovine serum (Gibco, NY, USA) and 10 U/ml penicillin/streptomycin.

For 3D sphere culture, SKOV3ip1 cells ($1 \times 10^6$) were dispensed on ultra-low adherent 6-well plate (Corning NY, USA), and then, cultured in 5% $CO_2$ incubator using RPMI 1640 medium supplemented with 10% fetal bovine serum (Gibco, NY, USA) and 10 U/ml penicillin/streptomycin (Gibco).

1.2 Morphological Analysis According to Culture Method

SKOV3ip1 ovarian cancer cells were divided and cultured by 2D monolayer cultures (2D MC) and 3D sphere cultured (3D SC), respectively. In order to observe whether different forms are present according to the culture methods, microscopic analysis was performed and results thereof are shown in FIG. 1 below.

As shown in FIG. 1, no aggregate was formed in 2D monolayer culture. However, 72 hours after 3D sphere culture, SKOV3ip1 ovarian cancer cells have formed aggregates in a loose sheet shape, which in turn were accumulated in a dense spheroid shape. From such results, it was demonstrated that 2D monolayer culture and 3D sphere culture may induce different forms of cells, and in particular, 3D sphere culture may reflect a metastatic type ovarian cancer which is present in a floating state in ascetic fluid in the abdominal cavity rather than an adhered state.

1.3 Analysis of Cell Survival Signal Change According to the Culture Method

In order to identify whether a change in signaling pathways associated with cell survival appears or not according to 2D monolayer culture (2D MC) and 3D sphere culture (3D SC), immunostaining was implemented. More particularly, after culturing SKOV3ip1 cells ($1 \times 10^6$) by 2D monolayer culture or 3D sphere culture described in section 1.1, expression of cell-signaling molecules including AKT, STAT3, p42/44 ERK and p38 MAPK was detected and activation states in the monolayer cultured cells and the sphere cultured cells were compared. The monolayer cultured or sphere cultured SKOV3ip1 cells were harvested and washed once with ice-cold 1× phosphate buffered saline, followed by dissolving the same in 100 µl ice-cold RIPA buffer (20 mM Tris-Cl, pH 8.0, 125 mM NaCl, 100 mM phenylmethylsulfonyl fluoride, 1 mM ethylene diamine tetraacetic acid, 1% Triton X-100, 0.5% sodium deoxycholate, 0.1% sodium dodecyl sulfate, 1× complete protease inhibitor cocktail (Roche, Mannheim, Germany)) on ice. After assessing the protein concentration using a Bradford Protein assay kit (Biorad, CA, USA), the same amount of proteins (30 µg) was separated by SDS-PAGE and moved to a nitrocellulose membrane, followed by immunostaining the same using a horseradish peroxide conjugated second antibody and a specific antibody. An immune activation band was detected with SuperSignal West Pico Chemiluminescent Substrate (Thermo, IL, USA) using a Fusion Solo chemiluminescence analyzer (Vilber Rourmat Marne la Vallee, France). Antibodies to STAT3 (H-190), STAT3 (B-7) phosphorylated at Tyr705 and actin (C-2) were purchased from Santa Cruz Biotechnology. Rabbit monoclonal antibodies on AKT, AKT (D9E) phosphorylated at Ser473, FGFR1 phosphorylated at Tyr 653/654, p42/44 MAPK, phosphorylated p42/44 MAPK, p38 MAPK and p38 MAPK phosphorylated at Tyr 180/182 were purchased from Cell Signaling Technology (MA, USA). Further, HRP-conjugated goat anti-mouse and rabbit secondary antibodies were purchased from Jackson Laboratories, while BGJ398 used in the experiment (against FGFR1/2/3) was purchased from Selleckchem (USA).

Figure 2:
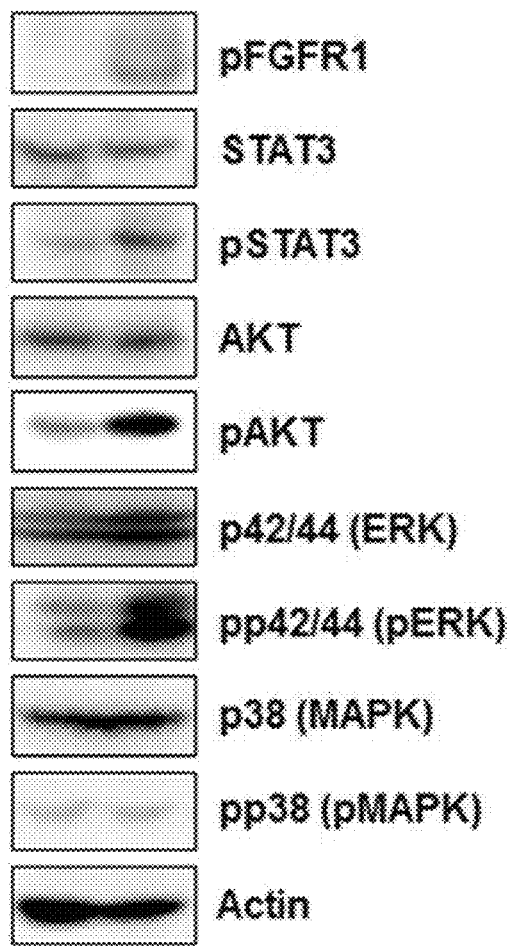
FIG. 2 is diagrams illustrating results of identifying expression of cell survival-related signaling molecules in cultured SKOV3ip1 ovarian cancer cells after 2-dimensional monolayer culture (2D MC) and 3-dimensional sphere culture (3D SC).

Expression of cell-signaling molecules involved in cell proliferation, which include AKT, STAT3, p42/44 ERK and p38 MAPK, were identified, and results of comparing activation states between the monolayer cultured cells and the sphere cultured cells are shown in FIG. 2.

As shown in FIG. 2, as a result of the immunostaining, it was determined that phosphorylation of p42/44 ERK, AKT and STAT3 was activated in the sphere cultured SKOV3ip1 cells rather than SKOV3ip1 cells cultured in 2D monolayer culture. Further, the phosphorylated FGFR1 was observed to have up-regulation in the sphere cultured SKOV3ip1 cells. Such results demonstrated that sphere culture conditions may lead up-regulation of a pro-survival signaling pathway in SKOV3ip1 cells, and further indicated that a spherical proliferation environment to embody metastasis micro-environments of the ovarian cancer cell line uses a signal mechanism of AKT and STAT3 in order to retain the cell viability of SKOV3ip1 cell line.

Up-regulation of the cell survival signaling pathway in the 3D sphere cultured SKOV3ip1 cells may reflect the ovarian cancer in a metastatic state, which exists in a survival state rather than a proliferation state, and is a result coincident with the morphological characteristics identified in Example 1.2 above.

Example 2. Reduction of Cell Viability of Sphere Cultured SKOV3ip1 Cells by BGJ398

In order to identify whether BGJ398 as a selective pan-FGFR inhibitor may influence upon SKOV3ip1 cells, SKOV3ip1 cells cultured in different culture environments were treated using BGJ398, followed by assessment of cell viability. Further, tyrosine kinase inhibitors such as TAE684 (NVP-TAE684, CAS 761439-42-3) and imatinib also known as gleevec, as well the standard anti-ovarian cancer chemotherapeutic agent, that is, paclitaxel were used to compare anti-tumor activity in SKOV3ip1 cells. TAE684 (against ALK) and imatinib (against Abl) used in the experiments were purchased from Selleckchem (USA), while AG490 (against JAK, CAS 133550-30-8) was purchased from Tocris (Bristol, UK).

Crystal violet staining was implemented to determine the cell viability in the monolayer cultured cell model and sphere cultured cell model. In order to implement the crystal violet staining in the monolayer culture model, SKOV3ip1 cells ($5 \times 10^4$) were dispensed in commercial 24-well plates and incubated overnight. Thereafter, the drug was dispensed with a desired concentration for experiment into each well, followed by further incubation for 72 hours. 300 µl of 0.2% crystal violet solution was added to each well, followed by further incubation for 20 minutes while gently stirring the same. The stained cells were washed with distilled water until a clean background is observed. For assessment using a colorimeter, the crystal violet dye was extracted with 1% SDS/PBS and absorbance was measured at 570 nm wavelength by EMax PLUS microplate reader (Molecular Device, USA).

In order to assess the cell viability in the sphere cultured cells, the SKOV3ip1 cells ($5 \times 10^4$) were dispensed on the super-low adherent 24-well plate and cultured overnight. The cells were harvested from each well and the commercial 24-well plate was moved, followed by further incubation for 12 hours. The adhered and visualized cells were stained with 0.2% crystal violet solution for 20 minutes while gently agitating the same. The stained cells were washed with distilled water until a clean background is observed. For assessment using a colorimeter, the crystal violet dye was extracted with 1% SDS/PBS and absorbance was measured at 570 nm wavelength by EMax PLUS microplate reader (Molecular Device, USA).

The monolayer cultured or sphere cultured SKOV3ip1 cells were treated with the tyrosine kinase inhibitor and paclitaxel for 72 hours, the cell viability was determined by the crystal violet colorimeter, and results thereof are shown in FIG. 3.

As shown in FIG. 3, the cell viability of the monolayer cultured SKOV3ip1 cells were reduced by paclitaxel and TAE648 in a dose-dependent manner. However, the cell viability of the monolayer cultured SKOV3ip1 cells was not effected by BGJ398 and imatinib. Especially, the sphere cultured SKOV3ip1 cells were observed to be more obviously resistant to paclitaxel than the monolayer cultured SKOV3ip1 cells, while TAE648 resistance was not identified in the sphere cultured SKOV3ip1 cells. Further, imatinib also did not affect the cell viability of the sphere cultured SKOV3ip1 cells. Meanwhile, BGJ398 exhibited different effects on the cell viability of SKOV3ip1 cells depending upon the monolayer culture or the sphere culture. More particularly, BGJ398 revealed cell apoptotic effects specific to the sphere cultured SKOV3ip1 cells at a very low temperature and reduced the cell viability in a dose-dependent manner.

Figure 4:
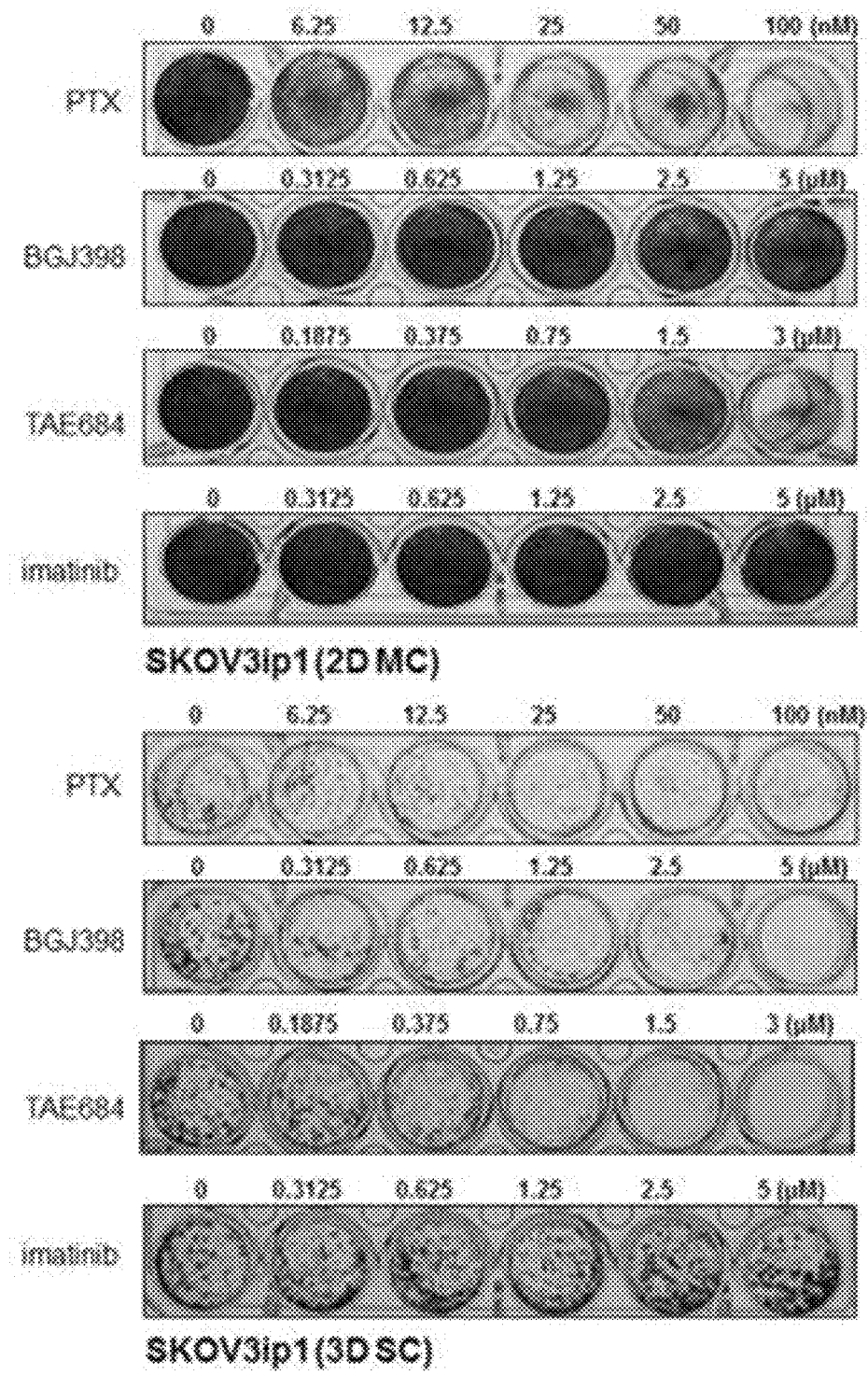
FIG. 4 is diagrams illustrating results of identifying cell viability through crystal violet staining, when cultured SKOV3ip1 ovarian cancer cells were treated with paclitaxel (PTX), BGJ398, TAE684 and imatinib, respectively, at different concentrations, after 2-dimensional monolayer culture (2D MC) and 3-dimensional sphere culture (3D SC)

Further, after treatment using paclitaxel or other different inhibitors, visualization results of 72-hour cell viability through crystal violet staining are shown in FIG. 4, and such results of observation of the crystal violet stained cells as shown in FIG. 4 also supported the colorimetric analysis result.

When the monolayer cultured SKOV3ip1 cells were treated using BGJ398, cytotoxicity was not revealed even with the increased concentration thereof to 5 μM. However, 3-dimensional sphere cultured SKOV3ip1 cells showed cytotoxicity at Day 3 even when the cells were treated with 1 μM BGJ398 only, and a dose-dependent increase in cytotoxicity was demonstrated. That is, BGJ398 did not exhibit anticancer activity in 2D monolayer cultured ovarian cancer cells reflecting attachable cancer, while exhibiting high anticancer activity specific to 3D sphere cultured ovarian cancer cells, i.e., the metastatic ovarian cancer cells.

Figure 5:
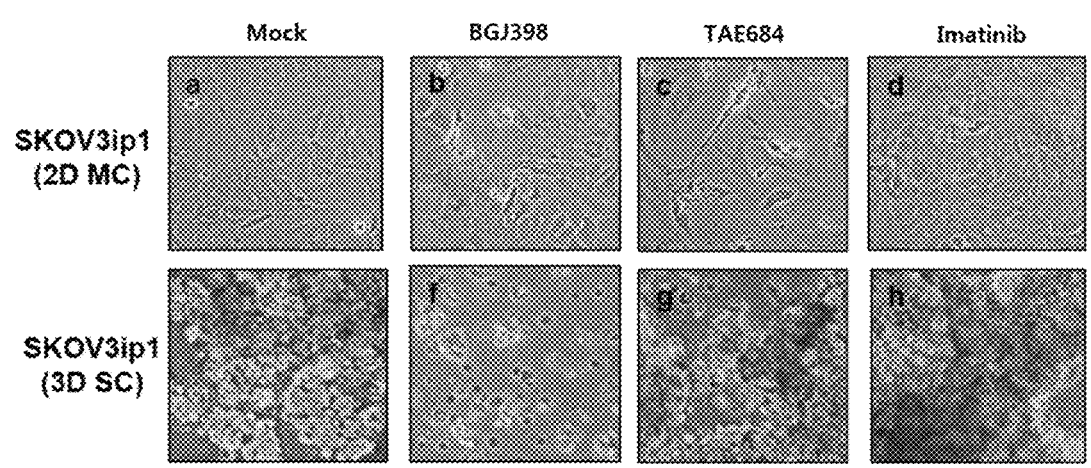
FIG. 5 is diagrams illustrating results of identifying the shape of cells, when cultured SKOV3ip1 ovarian cancer cells were treated with BGJ398, TAE684 and imatinib, respectively, after 2-dimensional monolayer culture (2D MC) and 3-dimensional sphere culture (3D SC).

Further, FIG. 5 shows results of identifying aggregated form of SKOV3ip1 cells in accordance with monolayer culture (2D MC), 3D sphere culture (3D SC), and 5 μM BGJ398 (BGJ), 3 μM TAE648 (TAE) and 5 μM imatinib (IMT) treatments.

As shown in FIG. 5, the sphere cultured SKOV3ip1 cells treated with BGJ398 did not retain a normal coagulation state. In contrast, spheroid degradation was not observed from the sphere cultured SKOV3ip1 cells with imatinib and TAE684 treatment. These results indicated that BGJ398 may be a potential chemical anticancer therapeutic agent for metastatic ovarian cancer SKOV3ip1 cells forming a spheroid, and also demonstrated that this may induce specific cytotoxicity in sphere culture reflecting metastatic microenvironments for ovarian cancer.

Example 3. Identification of AKT and STAT3 Phosphorylation Inhibitory Effect of BGJ398

BGJ398 was demonstrated to have specifically excellent anticancer activity in sphere culture as metastatic microenvironment in Example 2. Under this ground, in order to determine what types of cell signaling mechanisms are used to induce specific cytotoxicity by BGJ398 in sphere culture environment, expression and activity of various factors involved in cell survival and proliferation were examined through Western blotting.

In the sphere cultured SKOV3ip1 cells, Example 1 demonstrated that cell survival signaling molecules, that is, AKT and STAT3 were activated. Under this ground, in order to determine whether BGJ398 can vary the state of AKT and STAT3 in the sphere cultured SKOV3ip1 cells, the monolayer cultured (MC) or sphere cultured (SC) SKOV3ip1 cells were subjected to treatment using 5 μM BGJ398, followed by examining the degree of phosphorylation due to the above treatment.

Figure 6:
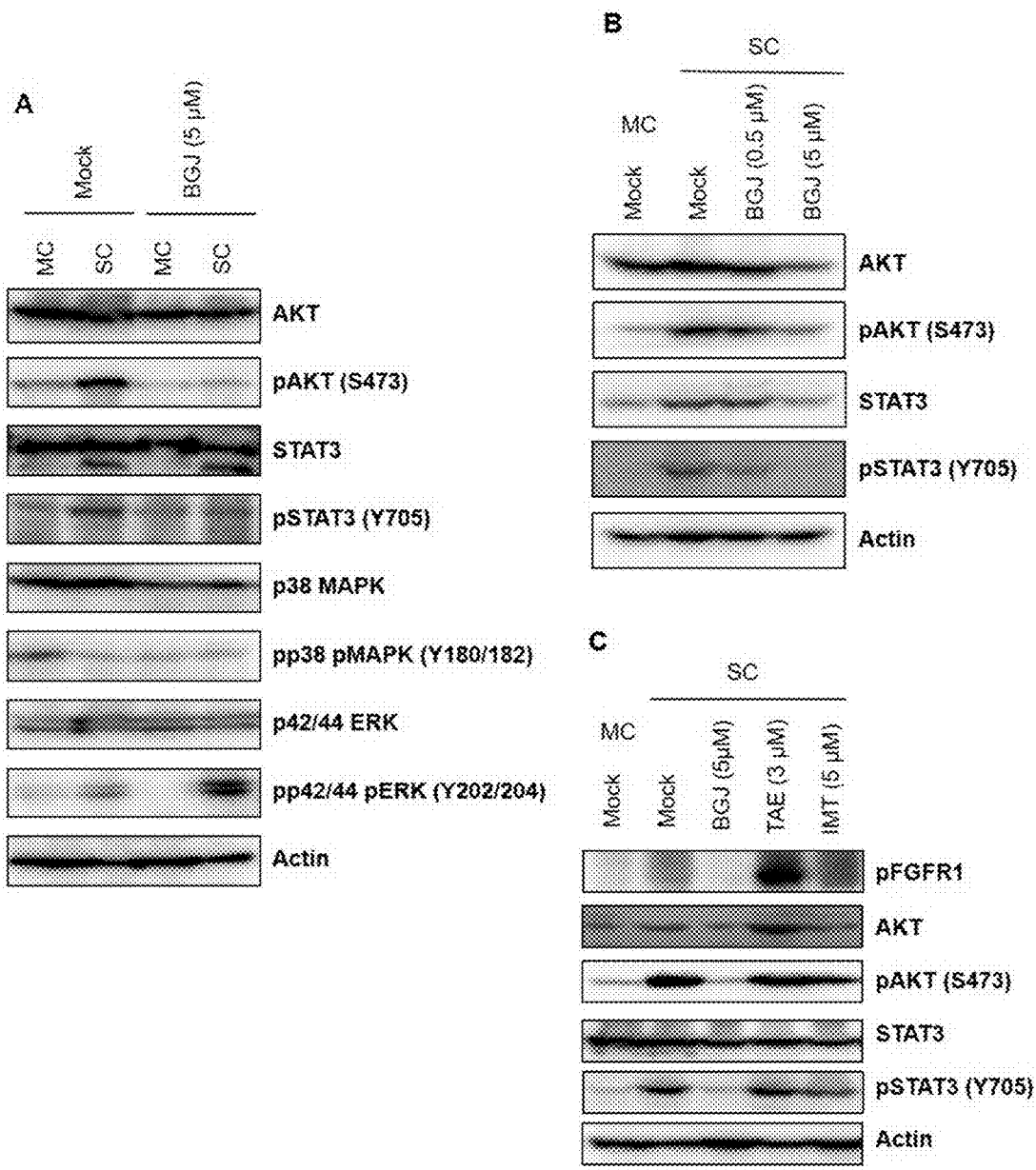
FIG. 6 is diagrams illustrating (A) results of identifying whether there is a change in phosphorylation of AKT and STAT3 as cell survival signaling molecules, obtained from treatment of cultured SKOV3ip1 ovarian cancer cells with BGJ398; and (B) and (C) results of identifying a change in phosphorylation of AKT and STAT3, when spherically cultured SKOV3ip1 was treated with 5 μM BGJ398 (BGJ), 3 μM TAE648 (TAE) and 5 μM imatinib (IMT), respectively, after 2-dimensional monolayer culture (2D MC) and 3-dimensional sphere culture (3D SC).

Further, the sphere cultured SKOV3ip1 cells were treated with 5 μM BGJ398 (BGJ), 3 μM TAE648 (TAE) and 5 μM imatinib (IMT), respectively. After 72 hours, a cell lysate was obtained and subjected to immunostaining, followed by analyzing active cellular expression of AKT and STAT3 with the antibody for the same. Further, a phosphorylation level of FGFR1 was used as a positive control group relative to BGJ treatment groups while actin was used as a loading control group. The analysis results are shown in FIG. 6. The immunostaining assay procedure was implemented in the same manner as in Example 1.

As shown in FIG. 6, the immunostaining assay results demonstrate that BGJ398 inhibits phosphorylated AKT at Ser473 residue in the sphere cultured SKOV3ip1 cells (A). Meanwhile, TAE684 and imatinib did not show such effects as described above (B). These results indicate that BGJ398 specifically inhibits AKT and STAT3 signaling pathway which was activated in the sphere cultured SKOV3ip1 cells rather than the monolayer cultured cells. That is, when the sphere cultured SKOV3ip1 cells were treated using BGJ398, it was determined that AKT and STAT3 phosphorylation activated during sphere culture is suppressed again. This result indicates that AKT and STAT3 phosphorylation activated in ovarian cancer metastasis environment is suppressed again through inhibition of FGFR signaling mechanism by BGJ398. In a case of 2-dimensional monolayer cultured SKOV3ip1, an increase in AKT and STAT3 phosphorylation was not observed and a reduction in phosphorylation and cytotoxicity by BGJ398 was also not revealed.

Since the cell survival of the sphere cultured SKOV3ip1 cells is inhibited by BGJ398 treatment, whether such cell survival inhibition is intermediated through JAK/STAT3 signaling pathway was further examined. For this purpose, the selective JAK tyrosine kinase inhibitor AG490 was used at different concentrations of 3.125 to 50 μM in order to treat the monolayer cultured or sphere cultured SKOV3ip1 cells, and after 72 hours, whether it affects the cell viability and AKT and STAT3 activation was examined through crystal violet staining and immunostaining assay, and results thereof are shown in FIG. 7. Actin was used as a loading control group.

As shown in FIG. 7, AG490 treatment did not suppress cell growth of the sphere cultured SKOV3ip1 cells (A). Further, AKT and STAT3 phosphorylation was also not inhibited by AG490 treatment on the sphere cultured SKOV3ip1 cells (B). Such results indicate that BGJ398 may efficiently suppress the cell growth of the sphere cultured SKOV3ip1 cells through inhibition of the major survival signaling molecules, i.e., AKT and STAT3, regardless of JAK/STAT3 signaling pathway.

Example 4. Identification of BGJ398 Efficacy on Cancer Cell Lines

With respect to the cancer cell lines listed in Table 1 below, synergistic effects of paclitaxel and BGJ398 were further examined. According to the same procedures as described in the previous examples, each cell line was divided and cultured by 2D monolayer culture and 3D sphere culture, respectively. Then, a change due to BGJ398 administration was analyzed through morphological analysis and crystal violet staining assay. All cell lines were purchased from ATCC and used in the present experiments, and detailed information thereof are shown in Table 3 below.

TABLE 1

| Cell line | Origin |
|---|---|
| HEC1B | Endometrial |
| Hs578T | Breast |

Figure 11:
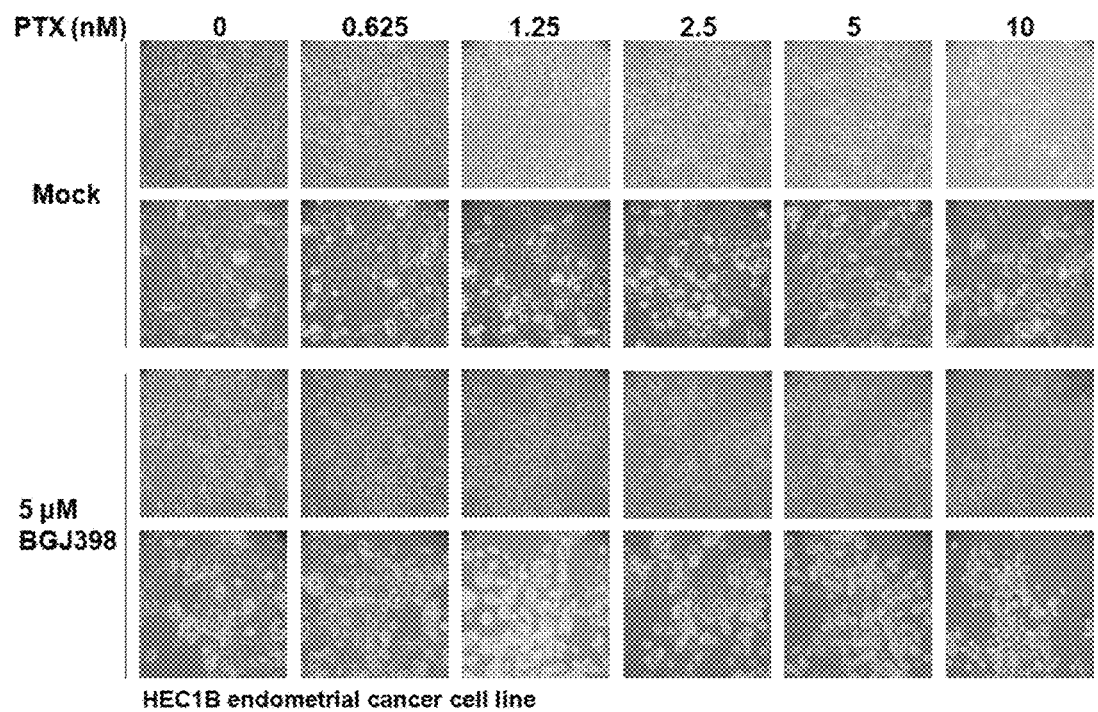
FIG. 11 is diagrams illustrating results of observation of a change in cell shape through a microscope, when HEC1B endometrial cancer cell line was treated with an anticancer drug paclitaxel at different concentrations in combination with BGJ398.
Figure 12:
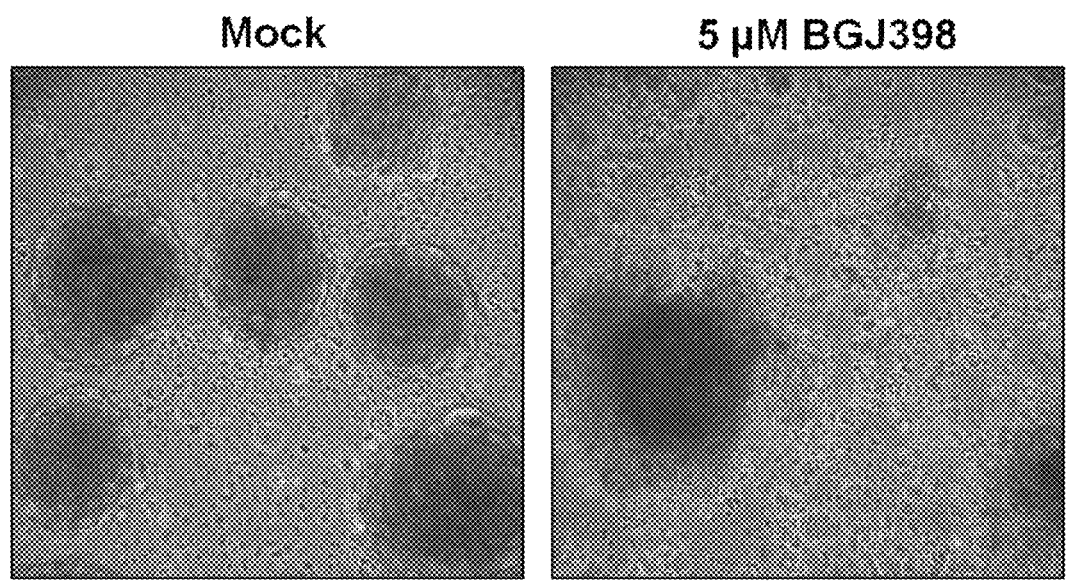
FIG. 12 is diagrams illustrating results of observation of the shape of cells through a microscope, when Hs578T breast cancer cell line was treated with BGJ398 after 3-dimensional sphere culture (3D SC).
Figure 13:
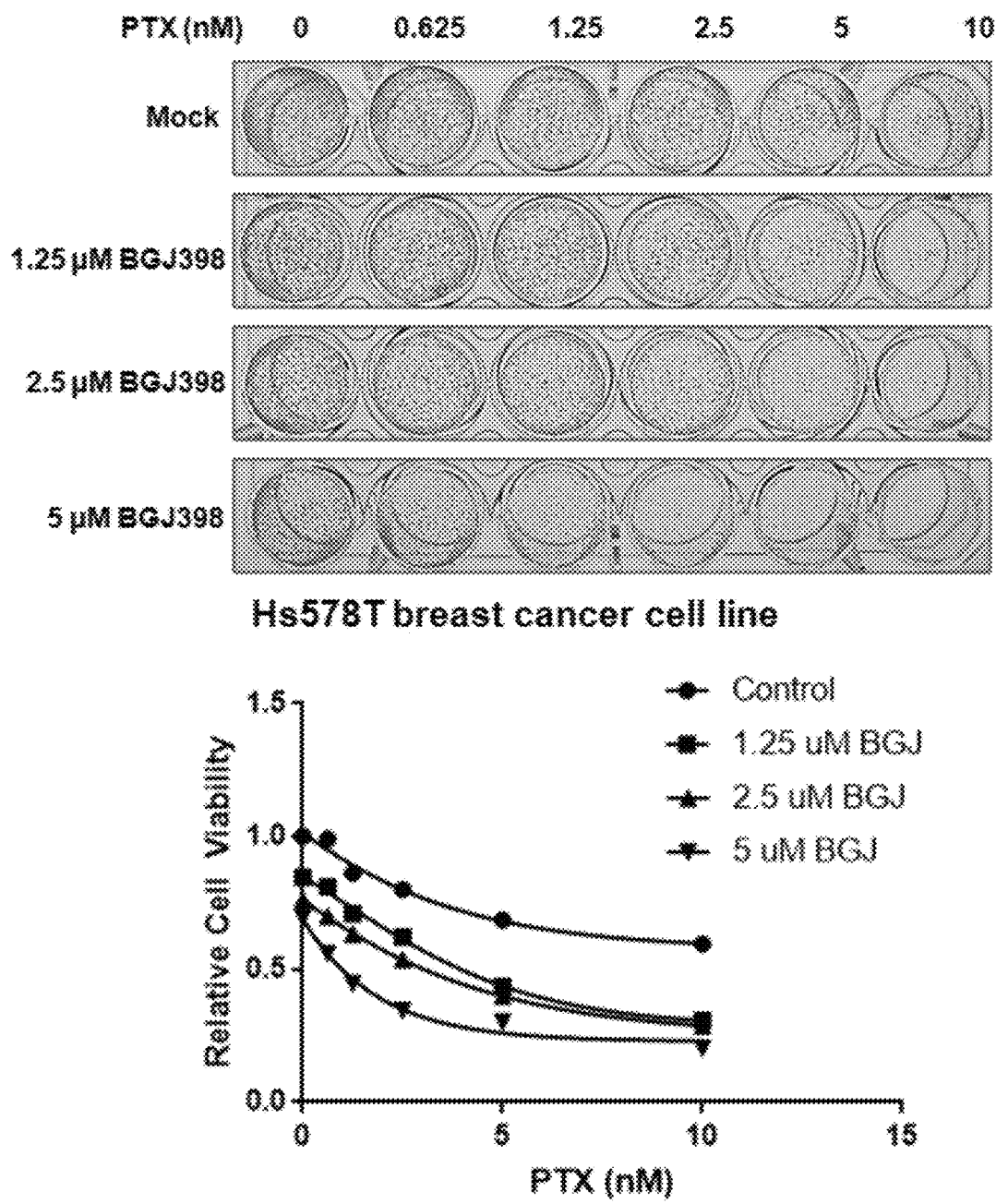
FIG. 13 is diagrams illustrating results of identifying cell apoptotic effects through crystal violet staining and graphs, when Hs578T breast cancer cell line was treated with an anticancer drug paclitaxel at different concentrations in combination with BGJ398.
Figure 14:
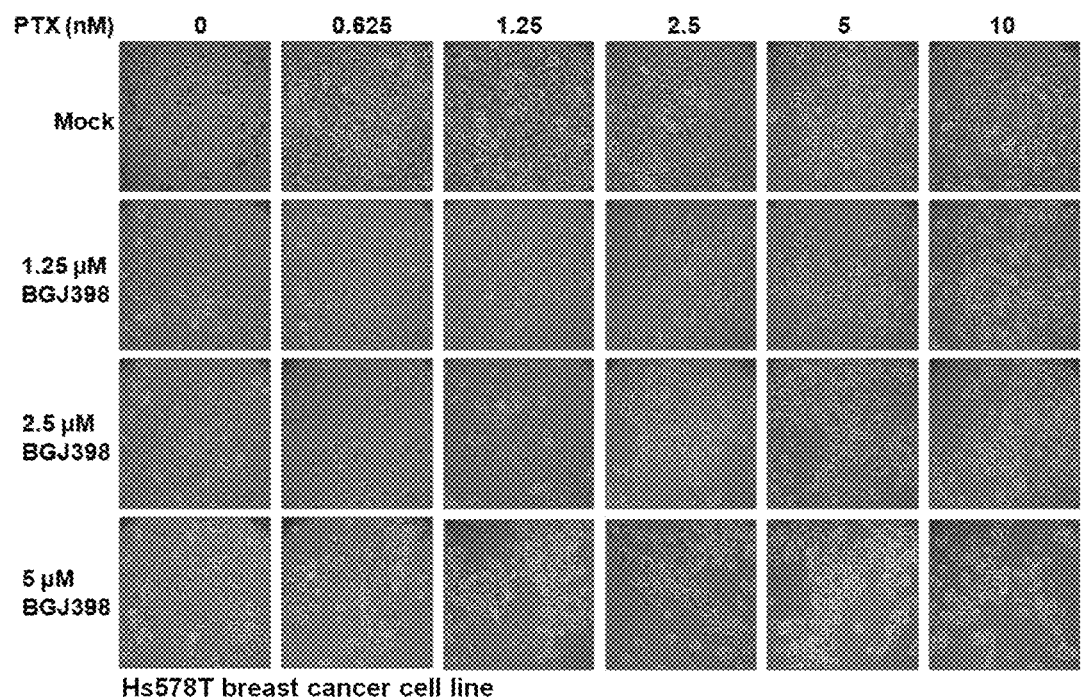
FIG. 14 is diagrams illustrating results of observation of a change in cell shape through a microscope, when Hs578T breast cancer cell line was treated with an anticancer drug paclitaxel at different concentrations in combination with BGJ398.

Results of the endometrial cancer cell line HEC1B are shown in FIGS. 9, 10 and 11, while results of the ovarian cancer cell line Hs578T are shown in FIGS. 12, 13 and 14.

Referring to FIGS. 9 to 12, upon BGJ398 administration, cell apoptosis can be found in the sphere cultured endometrial cancer cell line and breast cancer cell line, like SKOV (ovarian cancer) cell line.

Example 5. Identification of Synergistic Effect of Paclitaxel and BGJ398 on Each Cancer Cell Line 5.1 SKOV3ip1

It was demonstrated that BGJ398 could act as an effective anticancer drug to 3-dimensional sphere cultured ovarian cancer cells. Under this ground, when administering BGJ398 in combination with paclitaxel typically used as the existing primary anticancer drug for ovarian cancer, whether paclitaxel resistance of the sphere cultured cells is overcome and improved was determined. That is, in order to determine whether a combination of BGJ398 and paclitaxel exhibits synergistic effects in cell apoptosis of the sphere cultured SKOV3ip1 cells, the sphere cultured SKOV3ip1 cells were treated using a combination of continuously diluted paclitaxel and BGJ398 in different doses of 0, 1.25 and 5 5 µM, respectively. Then, after 72 hours, crystal violet colorimetric assay was implemented and results thereof are shown in FIG. 8.

As shown in FIG. 8, the sphere cultured SKOV3ip1 cells treated using paclitaxel in combination with BGJ398 were observed to have higher cell apoptosis than the cells treated with paclitaxel alone. More particularly, upon comparison between two experimental groups wherein one is 3D cultured SKOV3ip1 cells treated with paclitaxel alone at different concentrations ('BGJ398 untreated group'), and the other is the cells treated with 1.25 and 5 µM BGJ398, respectively ('BGJ398 treated group'), it was confirmed that the BGJ398 treated group has increased paclitaxel sensitivity in a dose-dependent manner, compared to the BGJ398 untreated group. Under this ground, it was identified that, when BGJ398 is administered in combination with paclitaxel, the sphere cultured SKOV3ip1 ovarian cancer cells could be efficiently killed. This indicates that inhibition of activity fibroblast growth factor using BGJ398 may be highly effective in suppressing proliferation of the metastatic ovarian cancer during 3-dimensional sphere culture which is metastatic micro-environments of the ovarian cancer. In other words, BGJ398 may exhibit effective anticancer ability in the sphere cultured ovarian cancer cells which may reflect a metastatic ovarian cancer state.

5.2 Other Cell Lines

With respect to the cancer cell lines listed in Table 2 below, synergistic effects of paclitaxel and BGJ398 were further examined. According to the same procedures as described in the previous examples, each cell line was divided and cultured by 2D monolayer culture and 3D sphere culture, respectively. Then, a change due to administration of BGJ398 alone or in combination with paclitaxel was analyzed through morphological analysis. In 3D sphere culture of both the endometrial cancer cell line HEC1B and the breast cancer cell line Hs578T cell line, it was observed cytotoxicity wherein cell spheres are collapsed to lead to unification of cells. As shown in FIGS. 10 and 13, in 2D monolayer culture of both the endometrial cancer cell line HEC1B and the breast cancer cell line Hs578T, it was determined that administration of BGJ398 in combination with paclitaxel allows BGJ398 to enhance anticancer effects of paclitaxel.

TABLE 2

| Cell line | Origin |
| --- | --- |
| HEC1B | Endometrial |
| Hs578T | Breast |

Results of HEC1B are shown in FIGS. 9, 10 and 11, while results of Hs578T are shown in FIGS. 12, 13 and 14.

Referring to FIGS. 9 to 13, upon administration of BGJ398 alone, cell apoptosis can be found in the sphere cultured endometrial cancer cell line and breast cancer cell line, like SKOV (ovarian cancer) cell line. Further, as shown in FIGS. 10 and 11, as well as FIGS. 13 and 14, upon administration of BGJ398 in combination with paclitaxel, it can be found that cell apoptosis is further increased.

In consideration of all these results, it is understood that: BGJ398 as a pan-FGFR inhibitor may be a therapeutic agent highly effective for metastatic ovarian cancer, endometrial cancer, breast cancer, etc.; and for targeting that FGFR may specifically serve to promote survival in maintaining the spheroid form of ovarian cancer cells, BGJ398 may accelerate degradation of spheroid in the metastatic ovarian cancer, thereby achieving cell apoptosis of the metastatic ovarian cancer.

Example 6. Identification of Synergistic Effects of Paclitaxel and BGJ398 on SKOV3/SKOV3-TR 6.1 Comparison of Paclitaxel Resistance of SKOV3/SKOV3-TR SKOV3-TR (Taxol resistant) includes SKOV3 ovarian cancer cell line as metrocyte and is a paclitaxel-resistant ovarian cancer cell line which was prepared by long term incubation using paclitaxel with the gradually increased concentration. SKOV3-TR cell line was offered from Sood AK in MD-Anderson Cancer Center (USA) and then used in the present experiments.

Paclitaxel resistance of each of SKOV3 and SKOV3-TR was determined by measuring the cell viability through crystal violet colorimetric assay. This experiment was implemented three times and a difference in results thereof was estimated by student's t-test.

Figure 15:
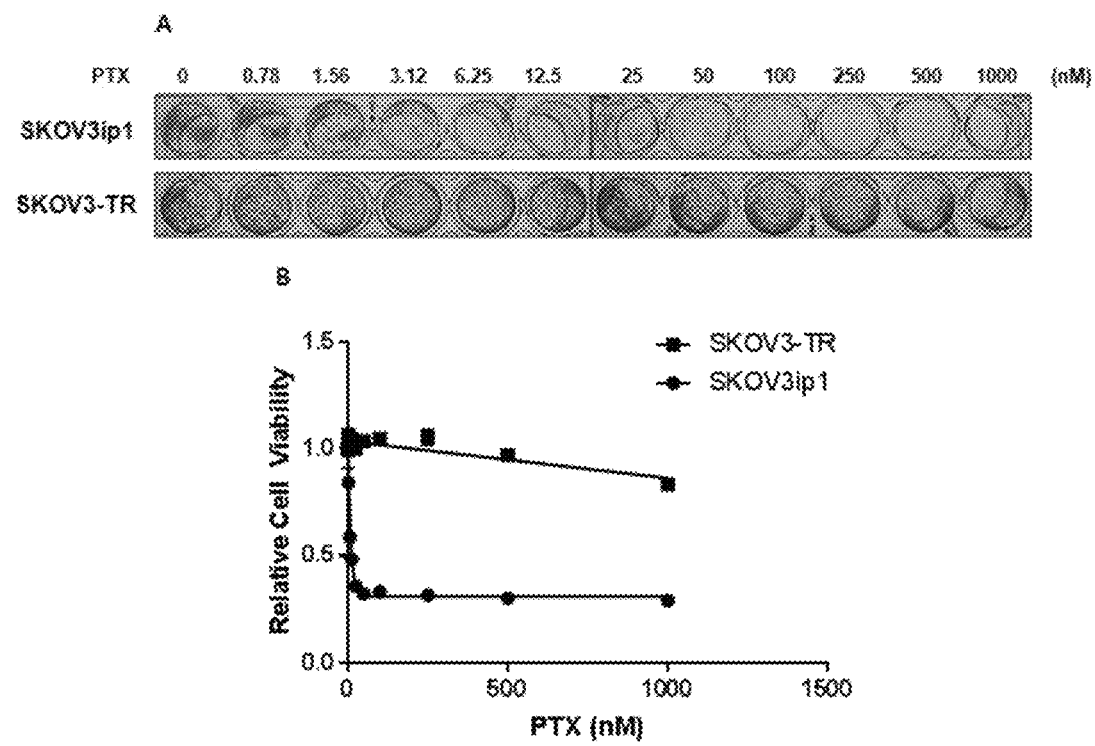
FIG. 15 illustrates resistance to paclitaxel ('paclitaxel resistance') in SKOV3 and SKOV3-TR, respectively.

Referring to FIG. 15, it could be seen that paclitaxel resistance of SKOV3-TR cell line is significantly higher than SKOV cell line.

6.2 Effects of promoting anticancer ability of paclitaxel by BGJ398 in paclitaxel-resistant cell line SKOV3-TR According to the same procedures as described in the previous examples, each cell line was divided and cultured by 2D monolayer culture and 3D sphere culture, respectively. Then, a change due to administration of BGJ398 alone or in combination with paclitaxel was analyzed through morphological analysis and crystal violet staining assay.

Figure 16:
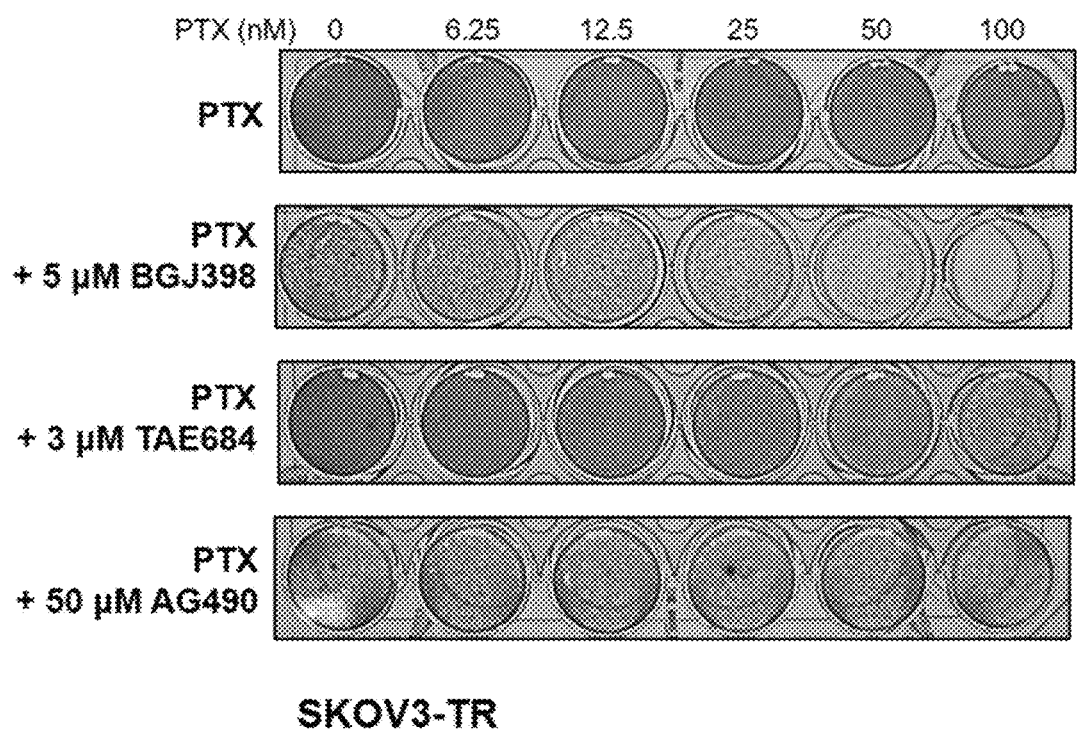
FIG. 16 illustrates a change in anticancer drug resistance due to various phosphorylation enzymes, that is, BGJ398, TAE648, AG490, in the anticancer drug paclitaxel-resistant ovarian cancer cell line SKOV3-TR. In particular, SKOV3-TR ovarian cancer cells were treated with paclitaxel (PTX) at different concentrations, and then, in combination with BGJ398, TAE684 and AG490, respectively, followed by visualization of cell viability through crystal violet staining.

FIG. 16 illustrates visualization of cell viability, resulting from treatment of SKOV3-TR ovarian cancer cells with paclitaxel (PTX) alone or in combination with BGJ398, TAE684 and AG490, respectively. Referring to this figure, it can be seen that anticancer activity is significantly improved by BGJ398 in combination with paclitaxel, compared to the treatment using paclitaxel alone.

Figure 17:
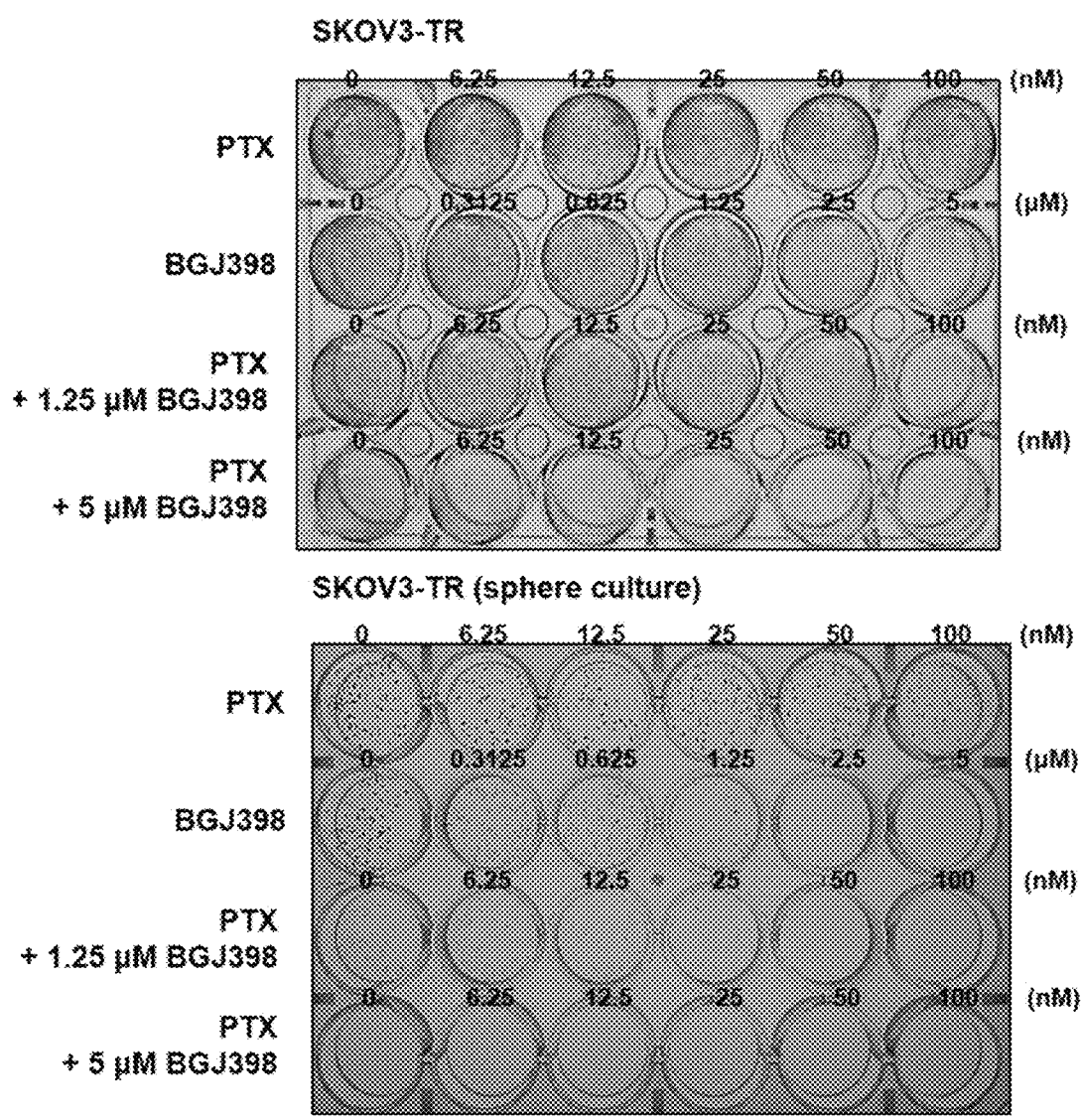
FIG. 17 illustrates visualization of concentration-dependent cell survival inhibitory effects of BGJ398 to paclitaxel through crystal violet staining, followed by comparison of the visualization results through graphical quantification, when paclitaxel alone, BGJ398 alone or in combination with paclitaxel was administered to the paclitaxel-resistant ovarian cancer cell line SKOV3-TR cells.

FIG. 17 illustrates cell viability, resulting from administration of paclitaxel alone, BGJ398 alone or in combination with paclitaxel to ovarian cancer cells after incubating paclitaxel-resistant cell line SKOV3-TR by 2D monolayer culture and 3D sphere culture, respectively. Referring to this figure, it can be seen that anticancer activity is more improved by administration of BGJ398 in combination with paclitaxel in the above both culture methods.

Figure 18:
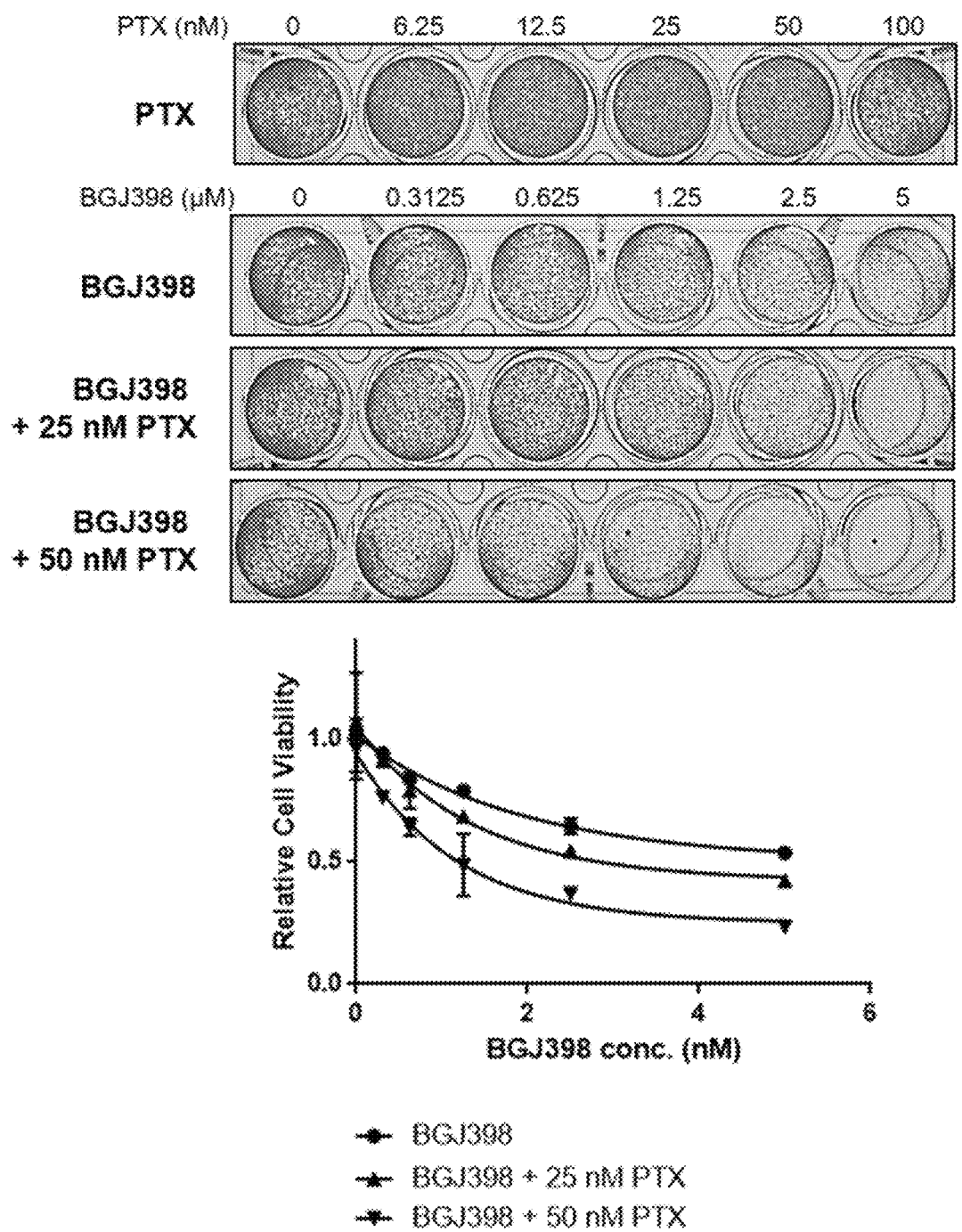
FIG. 18 illustrates comparison of visualization results of concentration-dependent cell survival inhibitory effects of paclitaxel to BGJ398 through crystal violet staining, when paclitaxel alone or in combination with BGJ398 was administered to the paclitaxel-resistant ovarian cancer cell line SKOV3-TR cells during 2D plain culture and 3D sphere culture, respectively.

FIG. 18 illustrates a result of determining whether BGJ398 has concentration-dependent anticancer effects on SKOV3-TR ovarian cancer cells in conjunction with use of paclitaxel. In particular, this figure illustrates cell viability resulting from administration of paclitaxel alone, BGJ398 alone or in combination with paclitaxel. Referring to this figure, it can be seen that anticancer activity is negligible by administration of paclitaxel alone, whereas administration of BGJ398 in combination with paclitaxel has blocked resistance, thereby attaining higher anticancer activity with the increased concentration of BGJ398.

Figure 19:
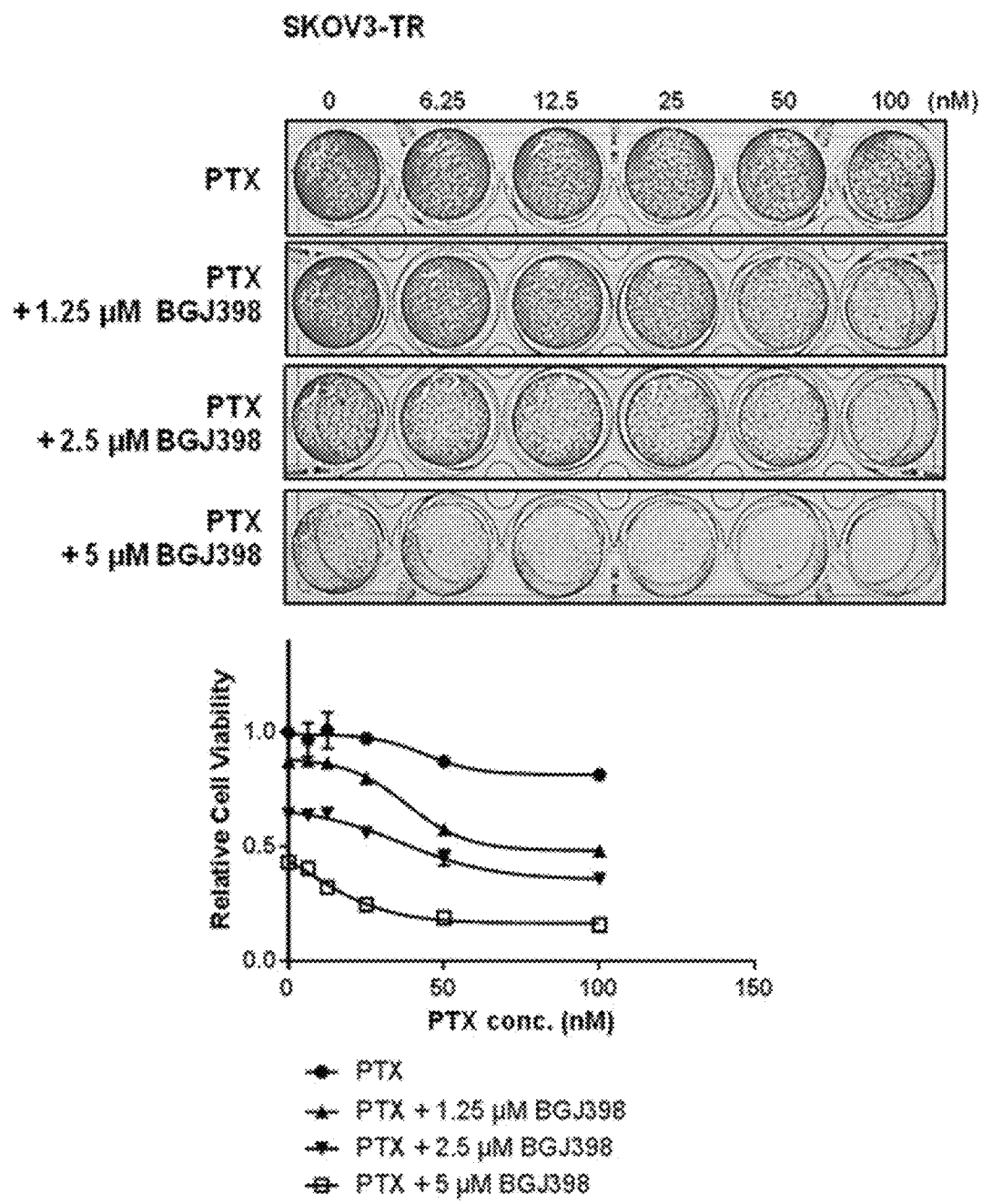
FIG. 19 illustrates visualization of concentration-dependent cell survival inhibitory effects of paclitaxel to BGJ398 through crystal violet staining, followed by comparison of the visualization results through graphical quantification, when paclitaxel alone or in combination with BGJ398 was administered to the paclitaxel-resistant ovarian cancer cell line SKOV3-TR cells.

FIG. 19 illustrates a result of determining whether paclitaxel has concentration-dependent anticancer effects on SKOV3-TR ovarian cancer cells in conjunction with use of BGJ398. In particular, this figure illustrates cell viability resulting from administration of paclitaxel alone, BGJ398 alone or in combination with paclitaxel. Referring to this figure, it can be seen that anticancer activity is negligible by administration of paclitaxel alone, whereas administration of BGJ398 in combination with paclitaxel has blocked resistance, thereby attaining higher anticancer activity with the increased concentration of paclitaxel.

Figure 20:
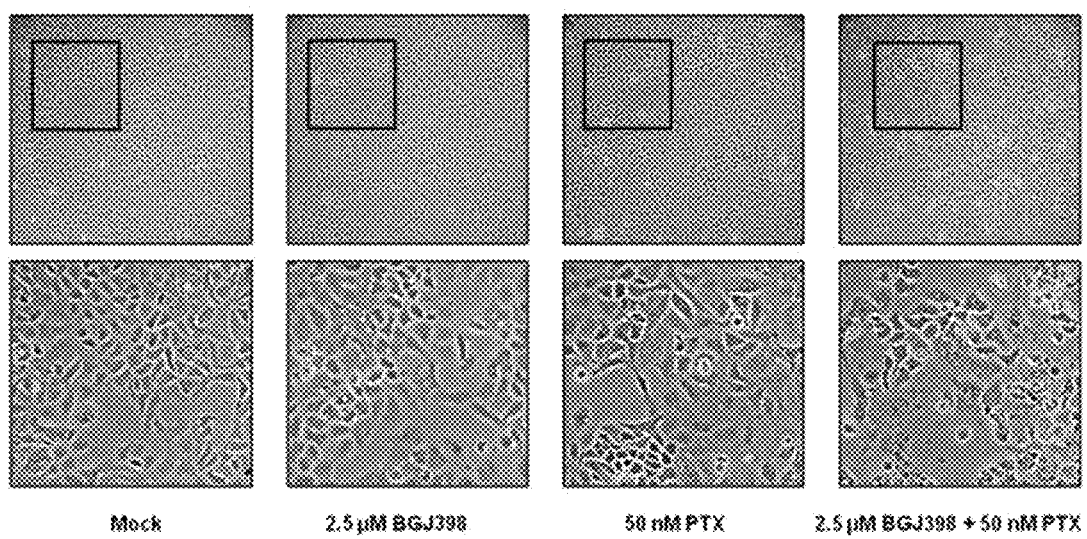
FIG. 20 illustrates a change in cell shape due to cytotoxicity under microscopic analysis, when paclitaxel alone, BGJ398 alone or in combination with paclitaxel was administered to the paclitaxel-resistant ovarian cancer cell line SKOV3-TR cells.

FIG. 20 illustrates a change in cell shape due to cytotoxicity under microscopic analysis, when paclitaxel alone, BGJ398 alone or in combination with paclitaxel was administered to SKOV3-TR ovarian cancer cells. For SKOV3-TR cells, it can be seen that both the treatment using 2.5 µM BGJ398 and the treatment using 50 nM paclitaxel exhibits negligible cytotoxicity and no morphological change, whereas the treatment using a combination of these two drugs reveals a detachment phenomenon due to cytotoxicity and formation of cells in irregular shapes.

Figure 21:
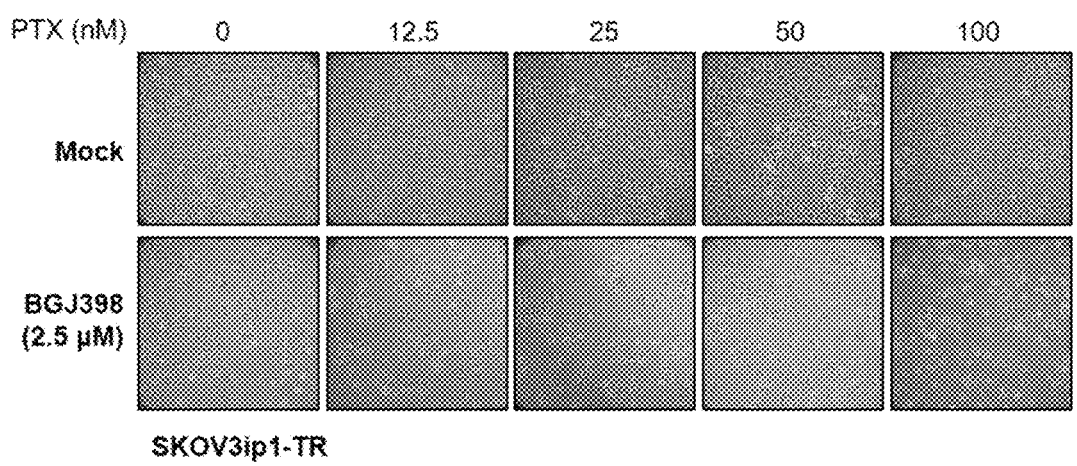
FIG. 21 illustrates a change in cell shape due to cytotoxicity under microscopic analysis, when paclitaxel alone at different concentrations or in combination with BGJ398 was administered to the paclitaxel-resistant cell line SKOV3ip1-TR which was prepared by treating SKOV3ip1 ovarian cancer cell line with the gradually increased concentration of paclitaxel.

In FIG. 21, the paclitaxel-resistant ovarian cancer cell line used herein was prepared from SKOV3ip1 cell line with the gradually increased concentrations of paclitaxel in the present laboratory. FIG. 21 illustrates a change in cell shape, when paclitaxel alone, BGJ398 alone or in combination with BGJ398 was administered to the SKOV3ip1-TR ovarian cancer cells. This figure shows that such a combination as described above can block paclitaxel resistance, thereby increasing anticancer activity.

Figure 22:
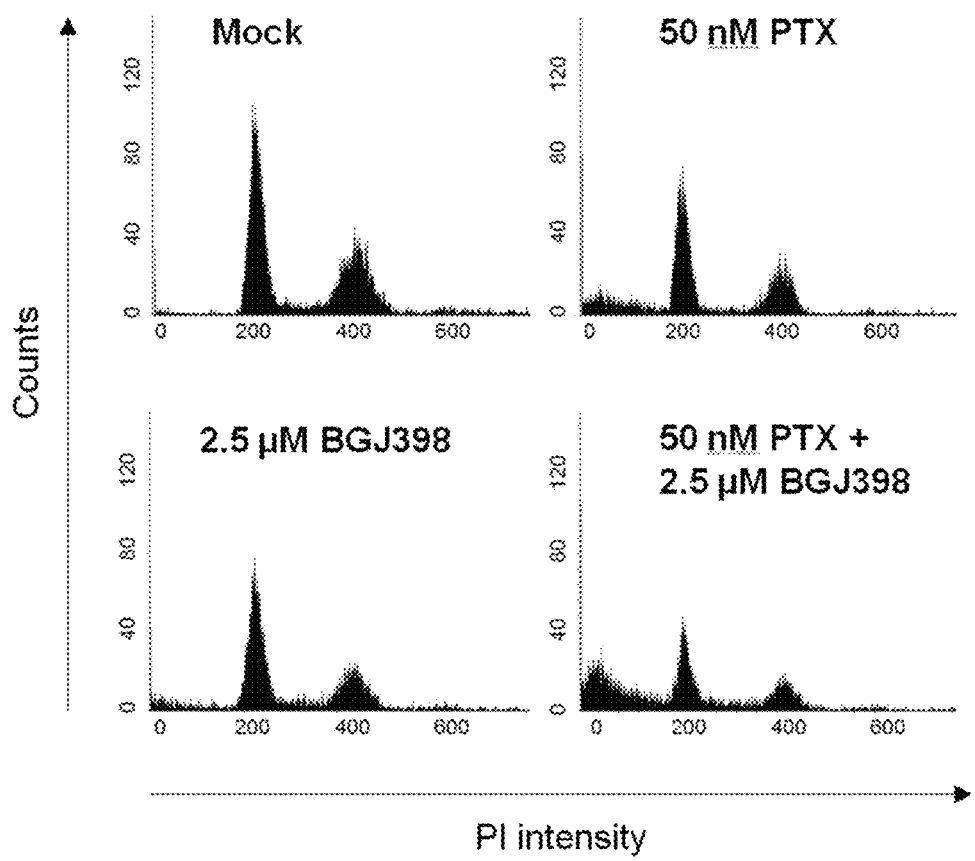
FIG. 22 illustrates cytotoxicity-derived cell apoptotic effects detected by measuring DNA content change through FACS, when paclitaxel alone, BGJ398 alone or in combination with paclitaxel was administered to the paclitaxel-resistant ovarian cancer cell line SKOV3-TR cells.

FIG. 22 illustrates an extent of cytotoxicity due to administration of paclitaxel alone, BGJ398 alone or in combination with paclitaxel to SKOV3-TR ovarian cancer cells, which was demonstrated by FACS assay. More particularly, the degree of cell apoptosis can be confirmed when DNA content in the cell is treated by propidium iodide (PI) staining and is assessed by FACS. If cell apoptosis occurs, genes in the cells are disrupted and Sub-Gi region below G1 is increased. Under this ground, it can be seen that the region below G1 is drastically increased and the number of apoptotic cells is increased by the treatment using BGJ398 in combination with paclitaxel (increase in Sub-G1)

Figure 23:
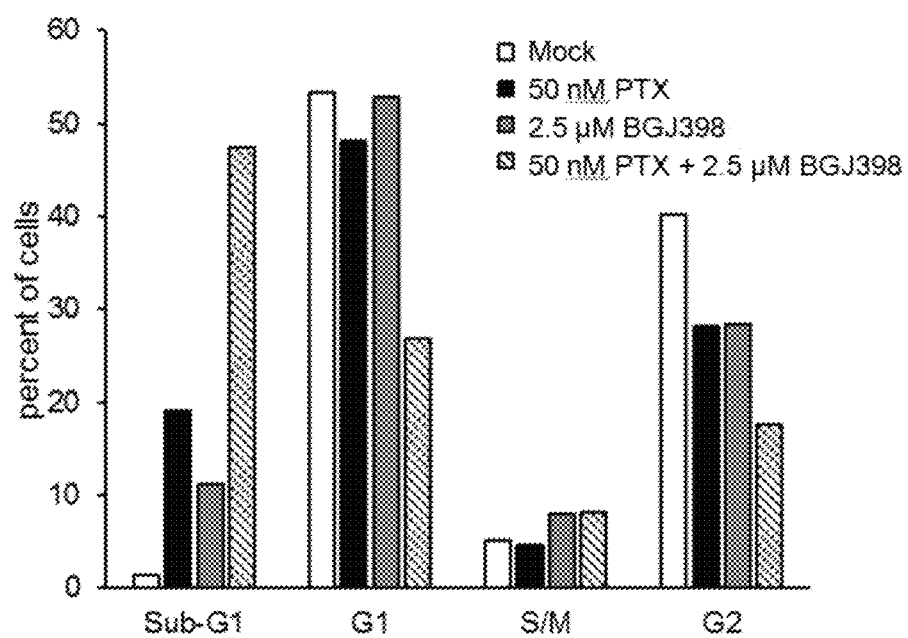
FIG. 23 illustrates comparison of cell apoptosis degree (Sub-G1) by graphically expressing results of FACS assay implemented in FIG. 21 in a cell cycle of Sub-G1, G1, S/M and G2.

FIG. 23 graphically illustrates FACS results, which were divided by a cell cycle in the same experiments described above. Referring to this figure, it can be seen that the treatment using 2.5 µM BGJ398 in combination with 50 nM paclitaxel increases Gub-G1 cells in SKOV-TR cells by about 2.5 times, compared to 50 nM paclitaxel alone, thereby improving anticancer activity.

Figure 24:
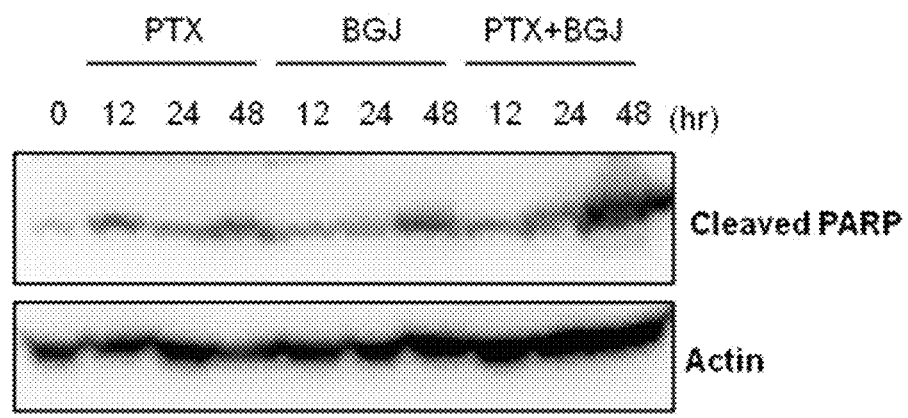
FIG. 24 illustrates results of identifying cell apoptotic effects over time through cleaved PARP and actin immunostaining, when paclitaxel alone, BGJ398 alone or in combination with paclitaxel was administered to SKOV3-TR ovarian cancer cells.
Figure 25:
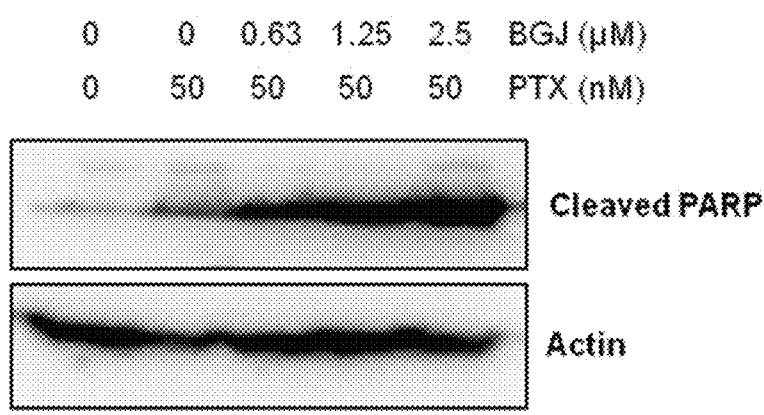
FIG. 25 illustrates concentration-dependent cell apoptotic effects of BGJ398 through cleaved PARP and actin immunostaining, when paclitaxel alone, BGJ398 alone or in combination with paclitaxel was administered to SKOV3-TR ovarian cancer cells.

FIGS. 24 and 25 illustrate expression of cleaved PARP and actin upon administration of paclitaxel alone, BGJ398 alone or in combination with paclitaxel to SKOV3-TR ovarian cancer cells, which was determined by the immunostaining method described above. Referring to these figures, it can be seen that the expression of cleaved PARP and actin is increased in concentration- and time-dependent manners by the treatment using BGJ398 in combination with paclitaxel.

Figure 26:
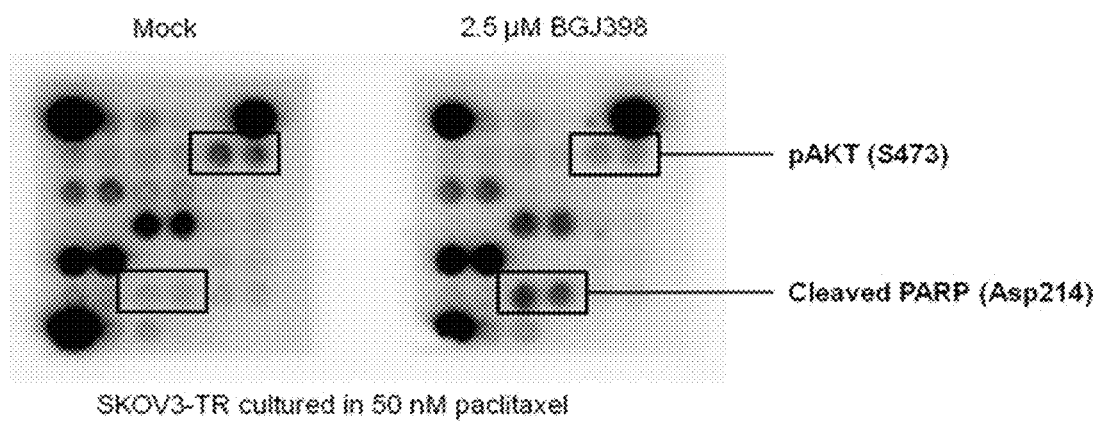
FIG. 26 illustrates results of identifying AKT phosphorylation inhibition and PARP cleavage induction by PathScan Intracellular Signaling Array Kit (Cell Signaling Technology), when paclitaxel alone or in combination with BGJ398 was administered to SKOV3-TR ovarian cancer cells.

FIG. 26 illustrates results of identifying AKT phosphorylation inhibition and PARP cleavage induction by PathScan Intracellular Signaling Array Kit (Cell Signaling Technology), when paclitaxel alone or in combination with BGJ398 was administered to SKOV3-TR ovarian cancer cells. From the figure, it can be seen that, upon administration of BGJ398 in combination with paclitaxel, phosphoylation of AKT at serine 473 is reduced while increasing the cleaved PARP.

Figure 27:
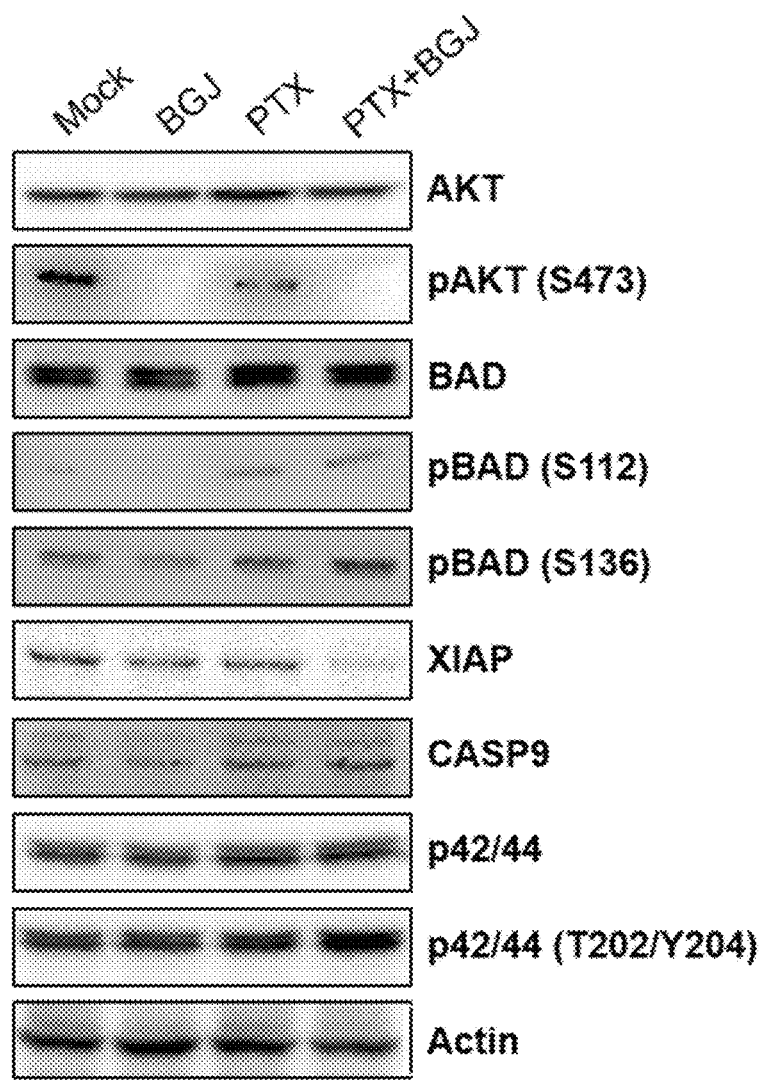
FIG. 27 illustrates results of identifying BAD phosphorylation, XIAP expression, CASP9 expression and p42/44 phosphorylation by immunostaining, which were known as down regulatory factors for apoptosis regulation due to a change in AKT activity within cells, when paclitaxel alone or in combination with BGJ398 was administered to SKOV3-TR ovarian cancer cells.

FIG. 27 illustrates results of identifying whether there is expression of AKT, phosphorylated AKT, BAD, phosphorylated BAD, XIAP, CASP9, p42/44 and/or phosphorylated p42/44, in order to determine AKT down-signal mechanism in relation to cell survival and cell apoptosis in the cells when paclitaxel alone or in combination with BGJ398 was administered to SKOV3-TR ovarian cancer cells. Referring to this figure, it can be seen that a level of phosphorylated AKT in SKOV3-TR cells is significantly decreased by BGJ398 treatment, and specifically, the XIAP expression is reduced. The reason of this fact is considered because a level of XIAP expression in the cells is decreased thus to improve paclitaxel sensitivity.

Figure 28:
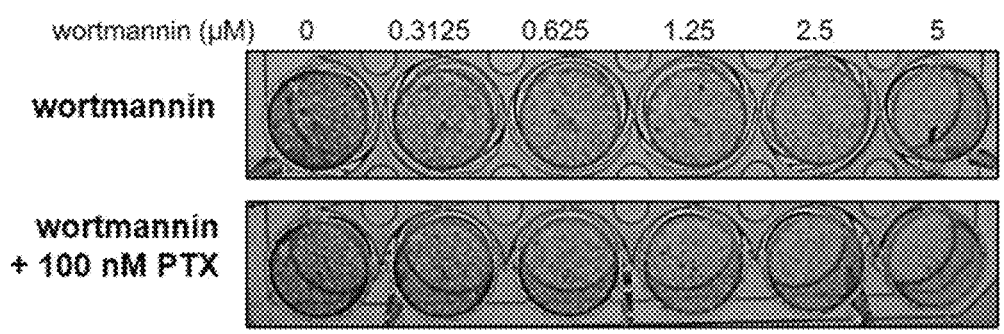
FIG. 28 illustrates results of identifying cell apoptotic effects of paclitaxel due to AKT inhibition through crystal violet staining assay, when paclitaxel alone or in combination with Wortmannin (CAS 19545-26-7) as AKT selective inhibitor was administered to SKOV3-TR ovarian cancer cells.

FIG. 28 illustrates a result of determining whether anticancer effects of paclitaxel is more or less improved in a concentration-dependent manner in SKOV3-TR cells by treating SKOV3-TR cells with wortmannin known as a PI3K/AKT inhibitor at different concentrations. This result indicates that AKT signaling mechanism is a very important regulatory factor in order to overcome the anticancer drug paclitaxel-resistance in SKOV3-TR cells.

Example 7. Identification of Synergistic Effects of Cisplatin and BGJ398 on SKOV3ip1/SKOV3-TR According to the same procedures as described in the previous examples, each cell line was subjected to 2D culture and a change thereof upon administration of cisplatin alone, BGJ398 alone or in combination with cisplatin was analyzed through crystal violet staining assay.

Figure 29:
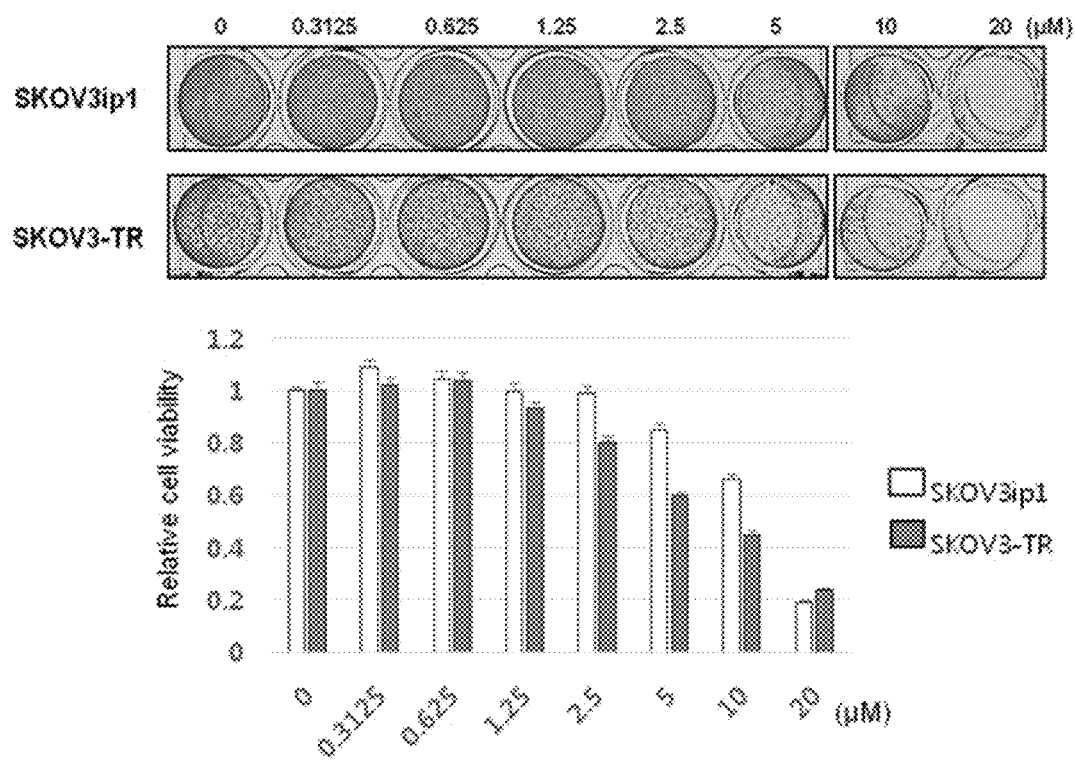
FIGS. 29 to 31 illustrate changes in SKOV3ip1 and SKOV3-TR due to administration of cisplatin alone, BGJ398 alone or in combination with cisplatin, which were analyzed through crystal violet staining assay.
Figure 30:
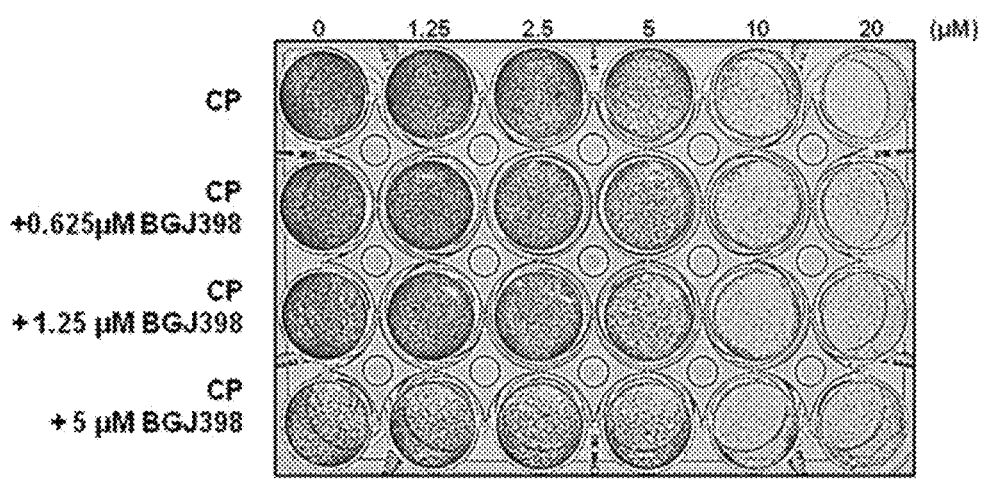
Figure 31:
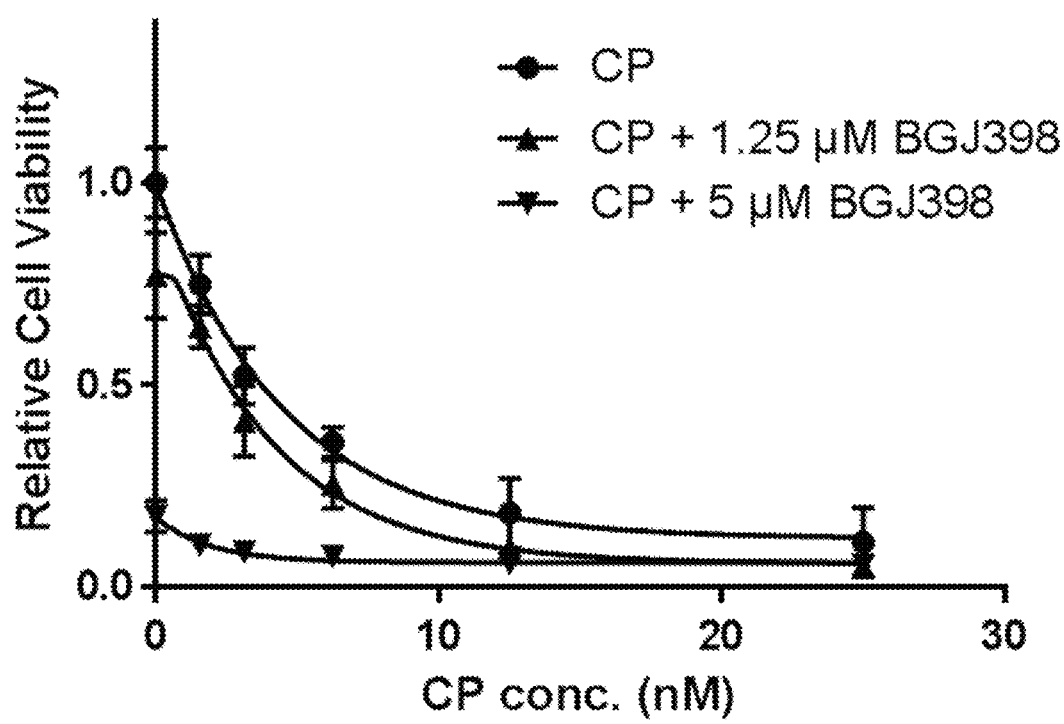

Referring to FIG. 29, it can be seen that both of SKOV3ip1 and SKOV3-TR exhibit sensitivity to cisplatin. Further, referring to FIGS. 30 and 31, it can be seen that anticancer activity is improved by administration of BGJ398 in combination with cisplatin.

The cell lines used in the above experiments are listed in Table 3 below.

TABLE 3

| Cell line | Origin | Description |
|---|---|---|
| OSE (ovarian surface epithelial cells) | Normal ovary epithelial cells | Offered by MD Anderson Cancer Center (Sood A) |
| SKOV3 | Epithelial ovarian adenocarcinoma | Offered by MD Anderson Cancer Center (Sood A) |
| SKOV3ip1 | SKOV3 | Obtained from SKOV3 Obtained from ascetic fluid of nude mice 7 weeks after peritoneal injection of SKOV3 Offered by MD Anderson Cancer Center (Sood A) |

TABLE 3-continued

| Cell line | Origin | Description |
|---|---|---|
| A2780 | Epithelial ovarian adenocarcinoma | Offered by MD Anderson Cancer Center (Sood A) |
| Hey AB | Epithelial ovarian carcinoma | Offered by MD Anderson Cancer Center (Sood A) |
| Hey AB-MIR | Epithelial ovarian carcinoma | Obtained from Hey AB Obtained by continuously exposing Hey AB to paclitaxel Offered by MD Anderson Cancer Center (Sood A) |
| SKOV3-TR | SKOV3 | Obtained from SKOV3 Obtained by continuously exposing SKOV3 to paclitaxel Offered by MD Anderson Cancer Center (Sood A) |
| SKOV3ip1-TR | SKOV3ip1 | Obtained from SKOV3ip1 Obtained by continuously exposing SKOV3ip1 to paclitaxel Offered by MD Anderson Cancer Center (Sood A) |

The invention claimed is:

1. A method for treatment of cancer in a spheroid form, the cancer selected from the group consisting of metastatic ovarian cancer, endometrial cancer, and breast cancer, the method comprising:
   administering a composition comprising at least one of a compound represented by Formula 1 and a pharmaceutically acceptable salt thereof to a subject in need thereof:

[Formula 1]

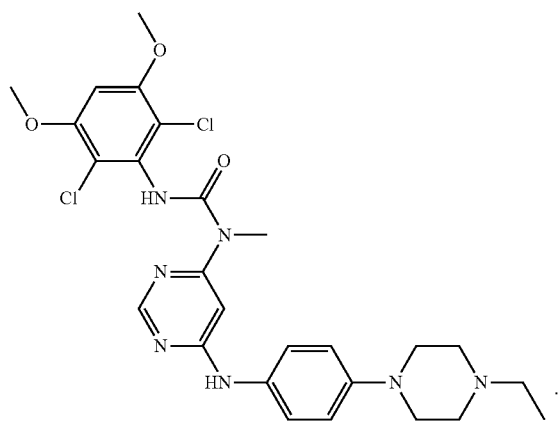

2. The method according to claim 1, wherein the cancer is the metastatic ovarian cancer that is stage III or stage IV ovarian cancer.

3. A method for treatment of cancer in a spheroid form selected from the group consisting of metastatic ovarian cancer, endometrial cancer, and breast cancer, wherein the cancer is resistant to paclitaxel, the method comprising administering a composition comprising at least one of a compound represented by Formula 1 and a pharmaceutically acceptable salt thereof to a subject in need thereof:

[Formula 1]

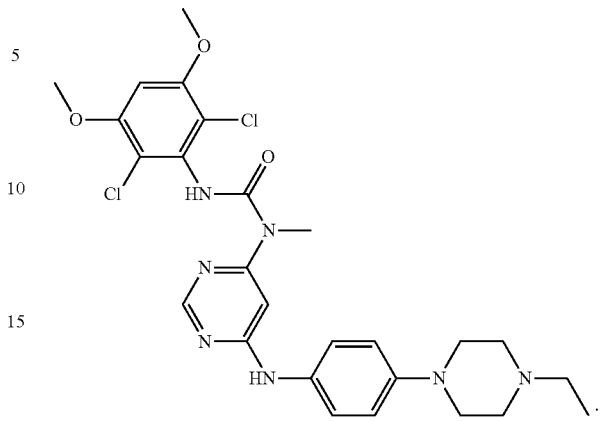

4. The method according to claim 1, wherein the compound represented by Formula 1 or the pharmaceutically acceptable salt thereof is administered in combination with a chemical anticancer agent.

5. The method according to claim 1, further comprising:
   before administering the composition, identifying chemical anticancer agent-resistance of the cancer of the subject; and
   administering the composition in combination with a chemical anticancer agent the subject if the subject is identified to acquire the chemical anticancer agent-resistance.

6. The method according to claim 4, wherein the chemical anticancer agent is an antimitotic agent or an alkylating agent.

7. The method according to claim 4, wherein the chemical anticancer agent includes paclitaxel.

8. The method of claim 1, wherein the cancer is the metastatic ovarian cancer.

9. The method of claim 1, wherein the cancer is the endometrial cancer.

10. The method of claim 1, wherein the cancer is the breast cancer.

11. The method of claim 4, wherein the chemical anticancer agent comprises an antimitotic agent.

12. The method of claim 11, wherein the antimitotic agent is selected from the group consisting of paclitaxel, docetaxel, vinblastine, vincristine, vinorelbine, colchicine, griseofulvin, and a combination thereof.

13. The method of claim 4, wherein the chemical anticancer agent comprises an alkylating agent.

14. The method of claim 13, wherein the alkylating agent comprises cisplatin.

15. The method of claim 1, further comprising administering a chemical anticancer agent before or after administering the composition.

16. A method for treatment of cancer in a spheroid form selected from the group consisting of metastatic ovarian cancer, endometrial cancer, and breast cancer, the method comprising:
   administering to a subject in need thereof a composition comprising:
   at least one of a compound represented by Formula 1 and a pharmaceutically acceptable salt thereof:

[Formula 1]
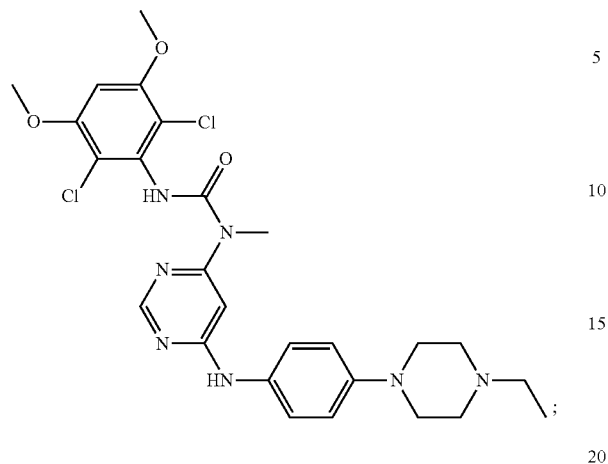
and
paclitaxel.
17. The method of claim 16, wherein the cancer is the metastatic ovarian cancer.
* * * * *